United States Patent
Kashiwamura et al.

(10) Patent No.: US 6,339,135 B1
(45) Date of Patent: *Jan. 15, 2002

(54) TRANSITION METAL COMPOUND, CATALYST FOR OLEFIN POLYMERIZATION, PROCESS FOR PREPARING OLEFIN POLYMER

(75) Inventors: Takashi Kashiwamura; Nobuhiro Yabunouchi; Masami Watanabe; Noriyuki Tani; Takuji Okamoto; Kiyohiko Yokota; Mitsugu Kanzawa; Tetsuya Inoue, all of Sodegaura (JP)

(73) Assignee: Idemitsu Kosan Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/913,364
(22) PCT Filed: Mar. 29, 1996
(86) PCT No.: PCT/JP96/00858
 § 371 Date: Sep. 29, 1997
 § 102(e) Date: Sep. 29, 1997
(87) PCT Pub. No.: WO96/30380
 PCT Pub. Date: Oct. 3, 1996

(30) Foreign Application Priority Data

Mar. 30, 1995 (JP) ................................. 7-74170

(51) Int. Cl.⁷ ........................... C08F 4/64; C08F 4/642; C07F 17/00
(52) U.S. Cl. ....................... 526/160; 502/103; 502/117; 556/53; 526/134; 526/161; 526/943
(58) Field of Search ................. 502/103, 117; 526/160, 943; 556/53

(56) References Cited

U.S. PATENT DOCUMENTS 5,496,902 A * 3/1996 Evertza et al. ............... 526/127
5,708,101 A * 1/1998 Bercaw et al. ............... 526/127
5,854,165 A * 12/1998 Yabunouchi et al. ....... 502/117

FOREIGN PATENT DOCUMENTS

WO   WO95/09172   * 4/1995

OTHER PUBLICATIONS

Mengele et al., ansa–Metallocene Derivatives 27: Chiral Zirconocene Complexes with Two Dimethylsiliylene Bridges, Organometallics 12, pp. 1931–1935, 1993.*
Cano et al., Double–Dimethylsilyl–Bridged Dicyclopentadienyl Group 4 Metal Complexes, Organometallics 13, pp. 1688–1694, 1994.*
Dorer et al., Syntheses and structure of Titanocene, Zirconocene, and Vanadocene Dichloride Complexes with Two Ethanediyl Bridges, Organometallics 13, pp. 3868–3872, 1994.*
Grossman et al., Synthesis and Structure of a C2–Symmetric, Doubly Bridged ansa–Titanocene Complex, Organometallics 13, pp. 3892–3896, 1994.*

* cited by examiner

Primary Examiner—David W. Wu
Assistant Examiner—R. Rabago
(74) Attorney, Agent, or Firm—Oblon, Spivak, McClelland, Maier & Neustadt, P.C.

(57) ABSTRACT

A novel double crosslinking type transition metal compound is herein disclosed which is represented by the general formula (I)

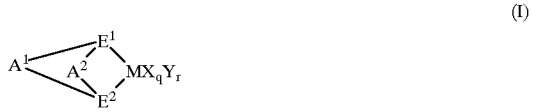

wherein M is a metallic element in the groups 3 to 10 or a lanthanoide series of the periodic table; $E^1$ and $E^2$ are each a cyclopentadienyl group, an indenyl group or the like, and they form a crosslinking structure via $A^1$ and $A^2$; $A^1$ and $A^2$ are each a crosslinking group comprising a hydrocarbon group of one or more carbon atoms; X is a σ-bonding ligand; and Y is a Lewis base. Also disclosed are a double crosslinking type biscyclopentadienyl derivative and bisindenyl derivative for use in the above-mentioned transition metal compound, its preparation process, a catalyst for olefin polymerization using the transition metal compound, and a preparation process of an olefin polymer by the use of this catalyst.

15 Claims, No Drawings

TRANSITION METAL COMPOUND, CATALYST FOR OLEFIN POLYMERIZATION, PROCESS FOR PREPARING OLEFIN POLYMER

TECHNICAL FIELD

The present invention relates to a transition metal compound, a double crosslinking type biscyclopenta-dienyl derivative and bisindenyl derivative for use in the transition metal compound, its preparation process, a catalyst for olefin polymerization using the transition metal compound, an olefin polymer obtained by the use of this catalyst, and a process for preparing the olefin polymer. More specifically, the present invention relates to a novel double crosslinking type transition metal compound useful as a component of a catalyst for olefin polymerization, a specific double crosslinking type biscyclopentadienyl derivative and bisindenyl derivative useful as a ligand of this transition metal compound, a process for efficiently preparing the double crosslinking type bisindenyl derivative, a catalyst for polymerization which has a high activity and an excellent copolymerizability and which contains the transition metal compound and which is capable of forming an olefin polymer having a uniform composition and a narrow molecular weight distribution, an olefin homopolymer and an olefin copolymer obtained by the use of this catalyst for polymerization, and a process for efficiently preparing the olefin polymer.

BACKGROUND ART

Heretofore, as highly active soluble catalysts for olefin polymerization, catalysts comprising a combination of a transition metal compound and an aluminoxane are known (Japanese Patent Application Laid-open Nos. 19309/1983 and 217209/1985). Furthermore, it has been reported that cationic species are useful as active species of the soluble catalyst for olefin polymerization [J. Am. Chem. Soc., Vol. 81, p. 81 (1959), Vol. 82, p. 1953 (1960), and Vol. 107, p. 7219 (1985)]. In addition, examples where each of these active species is isolated and is applied to the olefin polymerization have been described in J. Am. Chem. Soc., Vol. 108, p. 7410 (1986), Japanese PCT Patent Application Laid-open No. 502636/1989, Japanese Patent Application Laid-open No. 139504/1991, EP-A-O 468651 and the like. Other examples where this active species is used together with an organic aluminum compound have been described in Japanese Patent Application Laid-open No. 207704/1991, WO 92-1723 and the like. Moreover, an example of a catalyst for olefin polymerization which comprises a transition metal compound having a ligand containing an —SO$_3$R group and an organic aluminum oxycompound has been described in EP-A-O No. 519746 and the like.

However, these catalysts do not always satisfy a catalytic activity for olefin polymerization, copolymerizability, and the composition uniformity and the molecular weight distribution of an obtained polymer.

On the other hand, with regard to double cross-linking type metallocene complexes, "Organometallics", Vol. 12, p. 1931 (1993) has described a polymerization example of propylene in the presence of a dimethylsilylene double crosslinking type metallocene complex, but in order to obtain isotactic polypropylene by the utilization of this polymerization technique, the separation of a meso form of the metallocene complex from a racemic form thereof is required, and the heat stability of a catalyst itself is also poor.

Furthermore, the double crosslinking type metallocene complexes containing an ethylene crosslinking group has been suggested in "Organometallics", Vol. 13, p. 3868–3872 (1994), but in this case, a cyclopentadienyl group which can be used as a ligand does not have any substituent other than a crosslinking agent. Additionally, in its synthetic route, any product having a substituted cyclopentadienyl structure such as an indenyl group cannot be obtained.

DISCLOSURE OF THE INVENTION

The present invention has been intended under such circumstances, and an object of the present invention is to provide (1) a novel double crosslinking type transition metal compound (a double crosslinking type metallocene complex) useful as a component of a catalyst for olefin polymerization, (2) a double crosslinking type biscyclopentadienyl derivative and bisindenyl derivative usable as a ligand of this transition metal compound, (3) a process for efficiently preparing the double crosslinking type bisindenyl derivative, (4) a catalyst for polymerization which has a high activity and an excellent copolymerizability and which is capable of forming an olefin polymer having a uniform composition and a narrow molecular weight distribution, and (5) a process for efficiently preparing a catalyst by which a highly steric regular olefin polymer can be produced without requiring the division between a racemic form and a meso form.

The present inventors have intensively researched to achieve the above-mentioned object, and as a result, it has been found that a novel double crosslinking type transition metal compound having a specific structure is useful as a catalytic component for olefin polymerization; a specific double crosslinking type biscyclopentadienyl and bisindenyl derivative is useful as a ligand of the above-mentioned transition metal compound; and the double crosslinking type bisindenyl derivative can efficiently be prepared by a specific process.

Furthermore, the present inventors have found that a polymerization catalyst, which comprises the double crosslinking type transition metal compound, an activation cocatalyst, for example, a compound capable of reacting with the transition metal compound or its derivative to form an ionic complex, and if necessary, an organic aluminum compound, has a high activity and an excellent copolymerizability and can efficiently provide an olefin homopolymer or copolymer having a uniform composition and a narrow molecular weight distribution.

In consequence, the present invention has been completed on the above-mentioned findings.

That is to say, according to the present invention, there can be provided (1) a transition metal compound represented by the general formula (I)

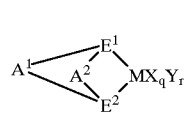

(I)

wherein N is a metallic element in the groups 3 to 10 or a lanthanoide series of the periodic table; $E^1$ and $E^2$ are each a ligand selected from the group consisting of a substituted cyclopentadienyl group, an indenyl group, a substituted indenyl group, a heterocyclopentadienyl group, a substituted heterocyclopentadienyl group, an amido group, a phosphide group, a hydrocarbon group and a silicon-containing group, and they form a crosslinking structure via $A^1$ and $A^2$, and they may be the same or different; X is a σ-bonding ligand, and when a plurality of Xs are present, these plural Xs may be the same or different, and each X may crosslink with another X, $E^1$, $E^2$ or Y; Y is a Lewis base, and when a plurality of Ys are present, these plural Ys may be the same or different, and each Y may crosslink with another Y, $E^1$, $E^2$ or X; $A^1$ and $A^2$ are each a crosslinking group comprising a hydrocarbon group of one or more carbon atoms, and they may be the same or different; q is an integer of 1 to 5 [(the valence of M)−2]; and r is an integer of 0 to 3, (2) a double crosslinking type biscyclopentadienyl derivative represented by the general formula (V)

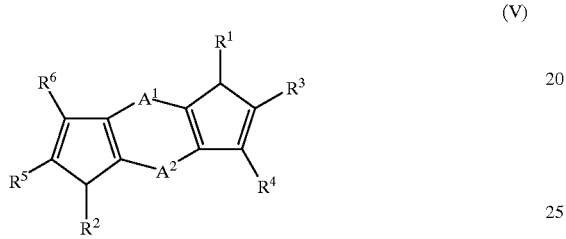

(V)

wherein $A^1$ and $A^2$ are as defined above; $R^1$ to $R^6$ are each a hydrogen atom, a halogen atom, a hydrocarbon group having 1 to 20 carbon atoms, or a halogen-containing hydrocarbon group having 1 to 20 carbon atoms, a silicon-containing group or a hetero-atom-containing group, but at least one of $R^1$ to $R^6$ is not a hydrogen atom, and they may be the same or different, and the adjacent groups of $R^1$ to $R^6$ may bond to each other to form a ring structure; and the positions of double bonds are not limited to the above, (3) a double crosslinking type bisindenyl derivative represented by the general formula (VII)

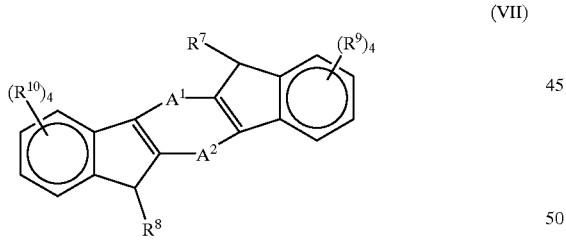

(VII)

wherein $A^1$ and $A^2$ are as defined above; $R^7$ to $R^{10}$ are each a hydrogen atom, a halogen atom, a hydrocarbon group having 1 to 20 carbon atoms, or a halogen-containing hydrocarbon group having 1 to 20 carbon atoms, a silicon-containing group or a hetero-atom-containing group, and they may be the same or different, and the adjacent groups of $R^7$ to $R^{10}$ may bond to each other to form a ring structure, and four $R^9$s may be the same or different, and four $R^{10}$s may be the same or different; and the positions of double bonds are not limited to the above, (4) a process for preparing a double crosslinking type bisindenyl derivative represented by the general formula (VII) which comprises the step of reacting a compound represented by the following general formula (VIII) with a base to carry out a coupling reaction:

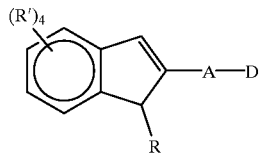

(VIII)

wherein R is $R^7$ or $R^8$; R' is $R^9$ or $R^{10}$; A is $A^1$ or $A^2$; $R^7$ to $R^{10}$ as well as $A^1$ and $A^2$ are as defined above, but the positions of double bonds are not limited to the above, (5) a catalyst for olefin polymerization which comprises a transition metal compound represented by the above-mentioned general formula (I) and an activation cocatalyst, (6) a catalyst for olefin polymerization which comprises (A) a transition metal compound represented by the above-mentioned general formula (I) and (B) a compound capable of reacting with the transition metal compound of the component (A) or its derivative to form an ionic complex, (7) a catalyst for olefin polymerization which comprises (A) a transition metal compound represented by the above-mentioned general formula (I) or (II), (B) a compound capable of reacting with the transition metal compound of the component (A) or its derivative to form an ionic complex, and (C) an organic aluminum compound, and (8) a process for preparing an olefin polymer which comprises the step of copolymerizing an olefin, another olefin and/or another monomer in the presence of a catalyst for olefin polymerization of the above-mentioned (5) to (7).

BEST MODE FOR CARRYING OUT THE INVENTION

Preferable embodiments of the present invention are (10) a transition metal compound represented by the general formula (I) which has a structure represented by the general formula (II)

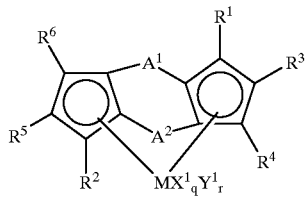

(II)

particularly the general formula (III)

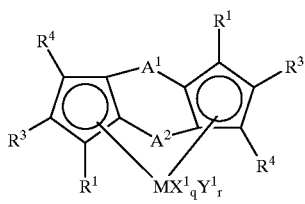

(III)

wherein M, $A^1$, $A^2$, $R^1$, $R^3$, $R^4$, q and r are as defined above; $X^1$ is a σ-bonding ligand, and when a plurality of $X^1$s are present, these plural $X^1$s may be the same or different, and each X may crosslink with another $X^1$ or $Y^1$; and $Y^1$ is a Lewis base, and when a plurality of $Y^1$s are present, these plural Ys may be the same or different, and each Y may crosslink with another $Y^1$ or $X^1$,

(11) a transition metal compound represented by the general formula (I) which has a structure represented by the general formula (IV)

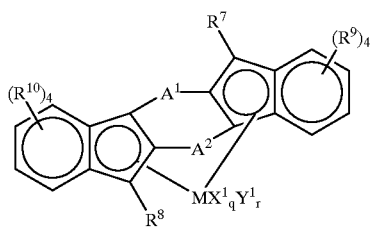

(IV)

wherein M, $A^1$, $A^2$, $R^7$ to $R^{10}$, $X^1$, $Y^1$, q and r are as defined above, and

(12) a double crosslinking type biscyclopentadienyl derivative represented by the general formula (V) which has a structure represented by the general formula (VI)

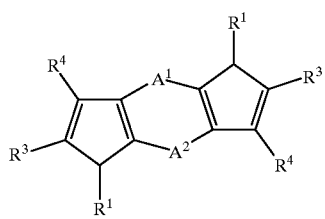

(VI)

wherein $A^1$, $A^2$, $R^1$, $R^3$ and $R^4$ are as defined above; but the positions of double bonds are not limited to the above.

A transition metal compound of the present invention is a novel double crosslinking type compound having a structure represented by the general formula (I):

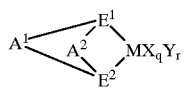

(I)

In the above-mentioned general formula (I), M is a metallic element in the groups 3 to 10 or a lanthanoide series of the periodic table, and typical examples of M include titanium, zirconium, hafnium, yttrium, vanadium, chromium, manganese, nickel, cobalt, palladium and lanthanoide metals. Above all, titanium, zirconium and hafnium are preferable from the viewpoint of an olefin polymerization activity. $E^1$ and $E^2$ are each a ligand selected from the group consisting of a substituted cyclopentadienyl group, an indenyl group, a substituted indenyl group, a heterocyclopentadienyl group, a substituted heterocyclo-pentadienyl group, an amido group (—N<), a phosphide group (—P<), a hydrocarbon group (>CR— or >C<) and a silicon-containing group (>SiR— or >Si<) (wherein R is hydrogen, a hydrocarbon group having 1 to 20 carbon atoms, or a hetero-atom-containing group), and they form a crosslinking structure via $A^1$ and $A^2$. Moreover, $E^1$ and $E^2$ may be the same or different. Preferably, $E^1$ and $E^2$ are each the substituted cyclopentadienyl group, the indenyl group or the substituted indenyl group.

Furthermore, X is a σ-bonding ligand, and when a plurality of Xs are present, these plural Xs may be the same or different, and each X may crosslink with another X, $E^1$, $E^2$ or Y. Typical examples of X include a halogen atom, a hydrocarbon group having 1 to 20 carbon atoms, an alkoxy group having 1 to 20 carbon atoms, an aryloxy group having 6 to 20 carbon atoms, an amido group having 1 to 20 carbon atoms, a silicon-containing group having 1 to 20 carbon atoms, a phosphide group having 1 to 20 carbon atoms, a sulfide group having 1 to 20 carbon atoms and an acyl group having 1 to 20 carbon atoms. On the other hand, Y is a Lewis base, and when a plurality of Ys are present, these plural Ys may be the same or different, and each Y may crosslink with another Y, $E^1$, $E^2$ or X. Typical examples of the Lewis base which is represented by Y include an amine, an ether, a phosphine and a thioether.

Next, $A^1$ and $A^2$ are each a crosslinking group comprising a hydrocarbon group having one or more carbon atoms, and they may be the same or different. Such a crosslinking group is represented by the general formula

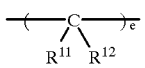

wherein $R^{11}$ and $R^{12}$ are each a hydrogen atom or a hydrocarbon group having 1 to 20 carbon atoms, and they may be the same or different and may bond to each other to form a ring structure; and e is an integer of 1 to 4.

Typical examples of the crosslinking group include a methylene group, an ethylene group, an ethylidene group, a propylidene group, an isopropylidene group, a cyclohexylidene group, a 1,2-cyclohexylene group and a vinylidene group ($CH_2=C=$). Above all, the methylene group, the ethylene group and the isopropylidene group are preferable. q is an integer of 1 to 5 and is [(the valence of M)-2]; and r is an integer of 0 to 3.

In the transition metal compound represented by the general formula (I), in the case that $E^1$ and $E^2$ are each the substituted cyclopentadienyl group, the indenyl group or the substituted indenyl group, the bonds of the double crosslinking groups of $A^1$ and $A^2$ may be present at (1,1') and (2,2') or at (1,2') and (2,1'). The preferable compound represented by the general formula (I) has, as the ligand, a double crosslinking type biscyclopentadienyl derivative represented by the general formula (II):

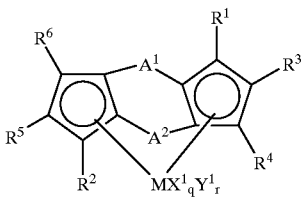
(II)

In the general formula (II), M, $A^1$, $A^2$, q and r are as defined above. $X^1$ is a σ-bonding ligand, and when a plurality of $X^1$s are present, these plural Xs may be the same or different, and each $X^1$ may crosslink with another $X^1$ or $Y^1$. Typical examples of $X^1$ include the same substances as exemplified in the description regarding X of the general formula (I). $Y^1$ is a Lewis base, and when a plurality of $X^1$s are present, these plural $X^1$s may be the same or different, and each $X^1$ may crosslink with another $Y^1$ or X. Typical examples of the Lewis base which is represented by $Y^1$ include the same substances as exemplified in the description regarding Y of the general formula (I). $R^1$ to $R^6$ are each a hydrogen atom, a halogen atom, a hydrocarbon group having 1 to 20 carbon atoms, or a halogen-containing hydrocarbon group having 1 to 20 carbon atoms, a silicon-containing group or a hetero-atom-containing group, but it is necessary that at least one of $R^1$ to $R^6$ should not be a hydrogen atom. Moreover, $R^1$ to $R^6$ may be the same or different, and the adjacent groups thereof may bond to each other to form a ring.

In the transition metal compound containing this double crosslinking type biscyclopentadienyl derivative as a ligand, the ligand may be a (1,1')(2,2') double crosslinking type or a (1,2') and (2,1') double crosslinking type.

Typical examples of the transition metal compounds represented by the general formula (I) of the present invention [the transition metal compounds represented by the general formulas (II), (III) and (IV) as well as other transition metal compounds] include (1,1'-ethylene)(2,2'-ethylene)-bis(indenyl)zirconium dichloride, (1,2'-ethylene)(2,1'-ethylene)-bis(indenyl)zirconium dichloride, (1,1'-methylene)(2,2'-methylene)-bis(indenyl)zirconium dichloride, (1,2'-methylene)(2,1'-methylene)-bis(indenyl)zirconium dichloride, (1,1'-isopropylidene)(2,2'-isopropylidene)-bis(indenyl)zirconium dichloride, (1,2'-isopropylidene)(2,1'-isopropylidene)-bis(indenyl)zirconium dichloride, (1,1'-ethylene)(2,2'-ethylene)-bis(3-methylindenyl)zirconium dichloride, (1,2'-ethylene)(2,1'-ethylene)-bis(3-methylindenyl)zirconium dichloride, (1,1'-ethylene)(2,2'-ethylene)-bis(4,5-benzoindenyl)zirconium dichloride, (1,2'-ethylene)(2,1'-ethylene)-bis(benzoindenyl)zirconium dichloride, (1,1'-ethylene)(2,2'-ethylene)-bis(4-isopropylindenyl)zirconium dichloride, (1,2'-ethylene)(2,1'-ethylene)-bis(4-isopropylindenyl)zirconium dichloride, (1,1'-ethylene)(2,2'-ethylene)-bis(5,6-dimethylindenyl)zirconium dichloride, (1,2'-ethylene)(2,1'-ethylene)-bis(5,6-dimethylindenyl)zirconium dichloride, (1,1'-ethylene)(2,2'-ethylene)-bis(4,7-diisopropyindenyl)zirconium dichloride, (1,2'-ethylene)(2,1'-ethylene)-bis(4,7-diisopropyindenyl)zirconium dichloride, (1,1'-ethylene)(2,2'-ethylene)-bis(4-phenylindenyl)zirconium dichloride, (1,2'-ethylene)(2,1'-ethylene)-bis(4-phenylindenyl)zirconium dichloride, (1,1'-ethylene)(2,2'-ethylene)-bis(3-methyl-4-isopropylindenyl)zirconium dichloride, (1,2'-ethylene)(2,1'-ethylene)-bis(3-methyl-4-isopropylindenyl)zirconium dichloride, (1,1'-ethylene)(2,2'-ethylene)-bis(5,6-benzoindenyl)zirconium dichloride, (1,2'-ethylene)(2,1'-ethylene)-bis(5,6-benzoindenyl)zirconium dichloride, (1,1'-ethylene)(2,2'-isopropylidene)-bis(indenyl)zirconium dichloride, (1,2'-ethylene)(2,1'-isopropylidene)-bis-(indenyl)zirconium dichloride, (1,1'-isopropylidene)(2,2'-ethylene)-bis(indenyl)zirconium dichloride, (1,2'-methylene)(2,1'-ethylene)-bis(indenyl)zirconium dichloride, (1,1'-methylene)(2,2'-ethylene)-bis(indenyl)zirconium dichloride, (1,1'-ethylene)(2,2'-methylene)-bis(indenyl)zirconium dichloride, (1,1'-methylene)(2,2'-isopropylidene)-bis(indenyl)zirconium dichloride, (1,2'-methylene)(2,1'-isopropylidene)-bis(indenyl)zirconium dichloride, (1,1'-isopropylidene)(2,2'-methylene)-bis(indenyl)zirconium dichloride, (1,1'-methylene)(2,2'-methylene)-bis(3-methylcyclopentadienyl) (cyclopentadienyl)zirconium dichloride, (1,1'-isopropylidene)(2,2'-isopropylidene)-(3-methylcyclopentadienyl)(cyclopentadienyl)zirconium dichloride, (1,1'-propylidene)(2,2'-propylidene)-(3-methylcyclopentadienyl)(cyclopentadienyl)zirconium dichloride, (1,1'-ethylene)(2,2'-ethylene)-bis(3-methylcyclopentadienyl)zirconium dichloride, (1,1'-methylene)(2,2'-ethylene)-bis(3-methylcyclopentadienyl)zirconium dichloride, (1,1'-isopropylidene)(2,2'-ethylene)-bis(3-methylcyclopentadienyl)zirconium dichloride, (1,1'-ethylene)(2,2'-isopropylidene)-bis(3-methylcyclopentadienyl)zirconium dichloride, (1,1'-methylene)(2,2'-ethylene)-bis(3-methylcyclopentadienyl)zirconium dichloride, (1,1'-methylene)(2,2'-isopropylidene)-bis(3-methylcyclopentadienyl)zirconium dichloride, (1,1'-isopropylidene)(2,2'-isopropylidene)-bis(3-methylcyclopentadienyl)zirconium dichloride, (1,1'-ethylene)(2,2'-methylene)-bis(3,4-dimethylcyclopentadienyl)zirconium dichloride, (1,1'-ethylene)(2,2'-isopropylidene)-bis(3,4-dimethylcyclopentadienyl)zirconium dichloride, (1,1'-methylene)(2,2'-methylene)-bis(3,4-dimethylcyclopentadienyl)zirconium dichloride, (1,1'-methylene)(2,2'-isopropylidene)-bis(3,4-dimethylcyclopentadienyl)zirconium dichloride, (1,1'-isopropylidene)(2,2'-isopropylidene)-bis(3,4-dimethylcyclopentadienyl)zirconium dichloride, (1,2'-ethylene)(2,1'-methylene)-bis(3-methylcyclopentadienyl)zirconium dichloride, (1,2'-ethylene)(2,1'-isopropylidene)-bis(3-methylcyclopentadienyl)zirconium dichloride, (1,2'-methylene)(2,1'-methylene)-bis(3-methylcyclopentadienyl)zirconium dichloride, (1,2'-methylene)(2,1'-isopropylidene)-bis(3-methylcyclopentadienyl)zirconium dichloride, (1,2'-isopropylidene)(2,1'-isopropylidene)-bis(3-methylcyclopentadienyl)zirconium dichloride, (1,2'-ethylene)(2,1'-methylene)-bis(3,4-dimethylcyclopentadienyl)zirconium dichloride, (1,2'-ethylene)(2,1'-isopropylidene)-bis(3,4-dimethylcyclopentadienyl)zirconium dichloride, (1,2'-methylene)(2,1'-methylene)-bis(3,4-dimethylcyclopentadienyl)zirconium dichloride, (1,2'-methylene)(2,1'-isopropylidene)-bis(3,4-dimethylcyclopentadienyl)zirconium dichloride, (1,2'-isopropylidene)(2,1'-isopropylidene)-bis(3,4-dimethylcyclopentadienyl)zirconium dichloride, and these compounds in which zirconium is replaced with titanium or hafnium. Needless to say, they are not restrictive. In addition, similar compounds containing metallic elements in other groups and a lanthanoide series of the periodic table are also usable.

The present invention is also directed to a double crosslinking type biscyclopentadienyl derivative represented by the general formula (V)

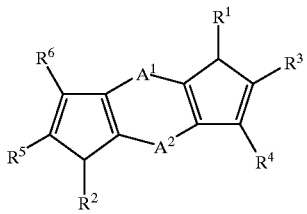

(V)

which can be used as a ligand of a transition metal compound represented by the general formula (II); a (1,2') and (2,1') double crosslinking type biscyclopentadienyl derivative represented by the general formula (VI)

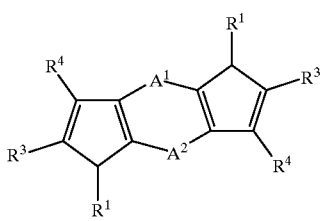

(VI)

[$A^1$, $A^2$, $R^1$ to $R^6$ are as defined above, but the positions of double bonds are not limited to the above] which can be used as a ligand of a transition metal compound represented by the general formula (III); and a (1,2') and (2,1') double crosslinking type biscyclopentadienyl derivative represented by the general formula (VII)

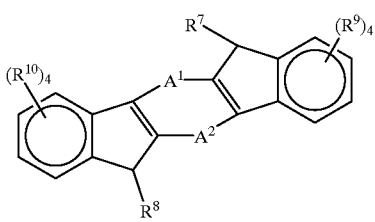

(VII)

[$A^1$, $A^2$, $R^7$ to $R^{10}$ are as defined above, but the positions of double bonds are not limited to the above] which can be used as a ligand of a transition metal compound represented by the general formula (IV).

Next, typical examples of the compounds [the double crosslinking type compounds represented by the general formulae (V), (VI) and (VII) as well as other double crosslinking type compounds] which can be used as the ligand of the transition metal compound represented by the general formula (I) include (1,1'-ethylene)(2,2'-ethylene)-bis(indene), (1,2'-ethylene)(2,1'-ethylene)-bis(indene), (1,1'-methylene)(2,2'-methylene)-bis(indene), (1,2'-methylene)(2,1'-methylene)-bis(indene), (1,1'-isopropylidene)(2,2'-isopropylidene)-bis(indene), (1,2'-isopropylidene)(2,1'-isopropylidene)-bis(indene), (1,1'-ethylene)(2,2'-ethylene)-bis(3-methylindene), (1,2'-ethylene)(2,1'-ethylene)-bis(3-methylindene), (1,1'-ethylene)(2,2'-ethylene)-bis(4,5-benzoindene), (1,2'-ethylene)(2,1'-ethylene)-bis(4,5-benzoindene), (1,1'-ethylene)(2,2'-ethylene)-bis(4-isopropylindene), (1,2'-ethylene)(2,1'-ethylene)-bis(4-isopropylindene), (1,1'-ethylene)(2,2'-ethylene)-bis(5,6-dimethylindene), (1,2'-ethylene)(2,1'-ethylene)-bis(5,6-dimethylindene), (1,1'-ethylene)(2,2'-ethylene)-bis(4,7-diisopropylindene), (1,2'-ethylene)(2,1'-ethylene)-bis(4,7-diisopropylindene), (1,1'-ethylene)(2,2'-ethylene)-bis(4-phenylindene), (1,2'-ethylene)(2,1'-ethylene)-bis(4-phenylindene), (1,1'-ethylene)(2,2'-ethylene)-bis(3-methyl-4-isopropylindene), (1,2'-ethylene)(2,1'-ethylene)-bis(3-methyl-4-isopropylindene), (1,1'-ethylene)(2,2'-ethylene)-bis(5,6-benzoindene), (1,2'-ethylene)(2,1'-ethylene)-bis(5,6-benzoindene), (1,1'-ethylene)(2,2'-isopropylidene)-bis(indene), (1,2'-ethylene)(2,1'-isopropylidene)-bis(indene), (1,1'-isopropylidene)(2,2'-ethylene)-bis(indene), (1,2'-methylene)(2,1'-ethylene)-bis(indene), (1,1'-methylene)(2,2'-ethylene)-bis(indene), (1,1'-ethylene)(2,2'-methylene)-bis(indene), (1,1'-methylene)(2,2'-isopropylindene)-bis(indene), (1,2'-methylene)(2,1'-isopropylindene)-bis(indene), (1,1'-isopropylidene)(2,2'-methylene)-bis(indene), (1,1'-methylene)(2,2'-methylene)(3-methylcyclopentadiene)(cyclopentadiene), (1,1'-propylindene)-(2,2'-propylindene)(3-methylcyclopentadiene)(cyclopentadiene), (1,1'-isopropylidene)(2,2'-isopropylindene)(3-methylcyclopentadiene)(cyclopentadiene), (1,1'-ethylene)(2,2'-methylene)-bis(3-methylcyclopentadiene), (1,1'-methylene)(2,2'-ethylene)-bis(3-methylcyclopentadiene), (1,1'-isopropylidene)(2,2'-ethylene)-bis(3-methylcyclopentadiene), (1,1'-ethylene)(2,2'-isopropylidene)-bis(3-methylcyclopentadiene), (1,1'-methylene)(2,2'-methylene)-bis(3-methylcyclopentadiene), (1,1'-methylene)(2,2'-isopropylidene)-bis(3-methylcyclopentadiene), (1,1'-isopropylidene)(2,2'-isopropylindene)-bis(3-methylcyclopentadiene), (1,1'-ethylene)(2,2'-methylene)-bis(3,4-dimethylcyclopentadiene), (1,1'-ethylene)(2,2'-isopropylidene)-bis(3,4-dimethylcyclopentadiene), (1,1'-methylene)(2,2'-methylene)-bis(3,4-dimethylcyclopentadiene), (1,1'-methylene)(2,2'-isopropylidene)-bis(3,4-dimethylcyclopentadiene), (1,1'-isopropylidene)(2,2'-isopropylidene)-bis(3,4-dimethylcyclopentadiene), (1,2'-ethylene)(2,1'-methylene)-bis(3-methylcyclopentadiene), (1,2'-ethylene)(2,1'-isopropylidene)-bis(3-methylcyclopentadiene), (1,2'-methylene)(2,1'-methylene)-bis(3-methylcyclopentadiene), (1,2'-methylene)(2,1'-isopropylidene)-bis(3-methylcyclopentadiene), (1,2'-isopropylidene)(2,1'-isopropylidene)-bis(3-methylcyclopentadiene), (1,2'-ethylene)(2,1'-methylene)-bis(3,4-dimethylcyclopentadiene), (1,2'-ethylene)(2,1'-isopropylidene)-bis(3,4-dimethylcyclopentadiene), (1,2'-methylene)(2,1'-methylene)-bis(3,4-dimethylcyclopentadiene), (1,2'-methylene)(2,1'-isopropylidene)-bis(3,4-dimethylcyclopentadiene) and (1,2'-isopropylidene)(2,1'-isopropylidene)-bis(3,4-dimethylcyclopentadiene).

The present invention is further directed to a process for preparing a double crosslinking type bisindenyl derivative represented by the above-mentioned general formula (VII).

This preparation process will be described as follows. A compound represented by the general formula (VIII)

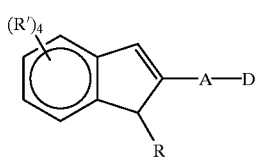
(VIII)

wherein R is $R^7$ or $R^8$; R' is $R^9$ or $R^{10}$; A is $A^1$ or $A^2$; $R^7$ to $R^{10}$ as well as $A^1$ and $A^2$ are as defined above; D is an elimination group such as a halogen atom, a tosyl group, a mesyl group or a brosyl group; but the positions of double bonds are not limited to the above, is reacted with a base, for example, a lithium salt such as lithium diisopropylamide or an amine such as triethylamine in a suitable solvent, for example, an ether such as diethyl ether, diisopropyl ether, di-n-butyl ether, 1,2-dimethoxyethane, 1,2-diethoxyethane or tetrahydrofuran, or a hydrocarbon such as n-butane, n-hexane, n-octane, toluene or xylene at a temperature of about −80 to 100° C., preferably −80 to 30° C. to carry out a coupling reaction, thereby obtaining a (1,2')(2,1') double crosslinking type bisindenyl derivative represented by the general formula (VII).

In the case that a product of the general formula (VII) having different $A^1$ and $A^2$ is prepared by this reaction, a compound of the general formula (VIII) having two different components of A should be used to conduct the coupling reaction.

The above-mentioned reaction can be shown by the following reaction formulae:

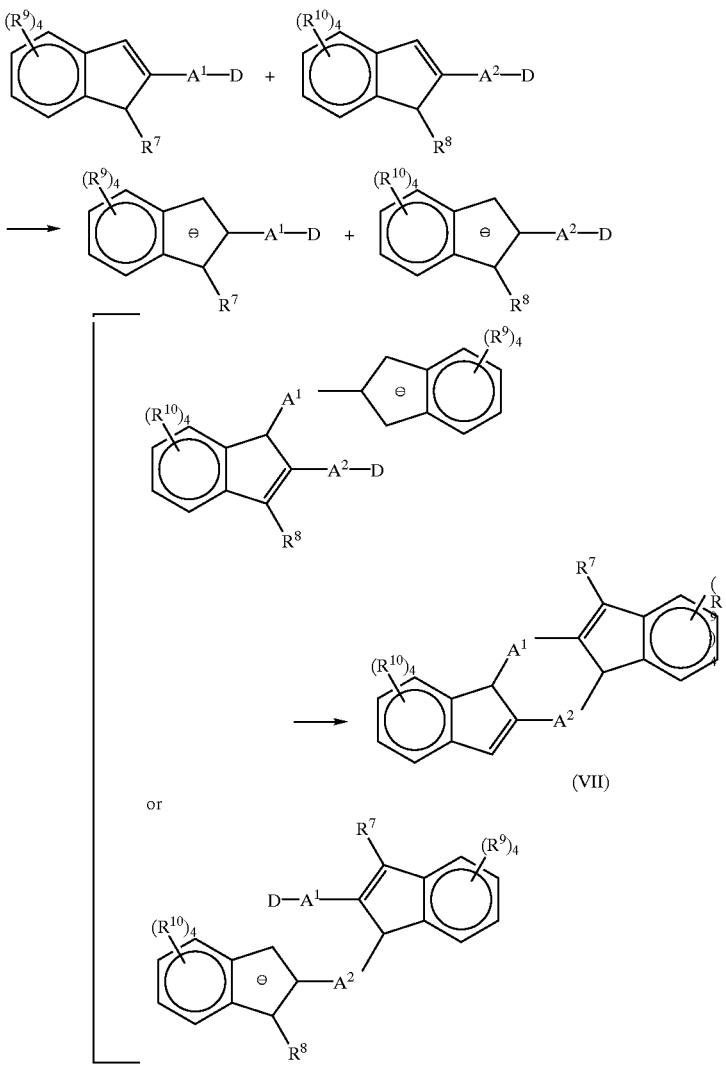

Furthermore, a (1,1')(2,2') double crosslinking type bisindenyl derivative can be prepared in accordance with the following reaction formulae:

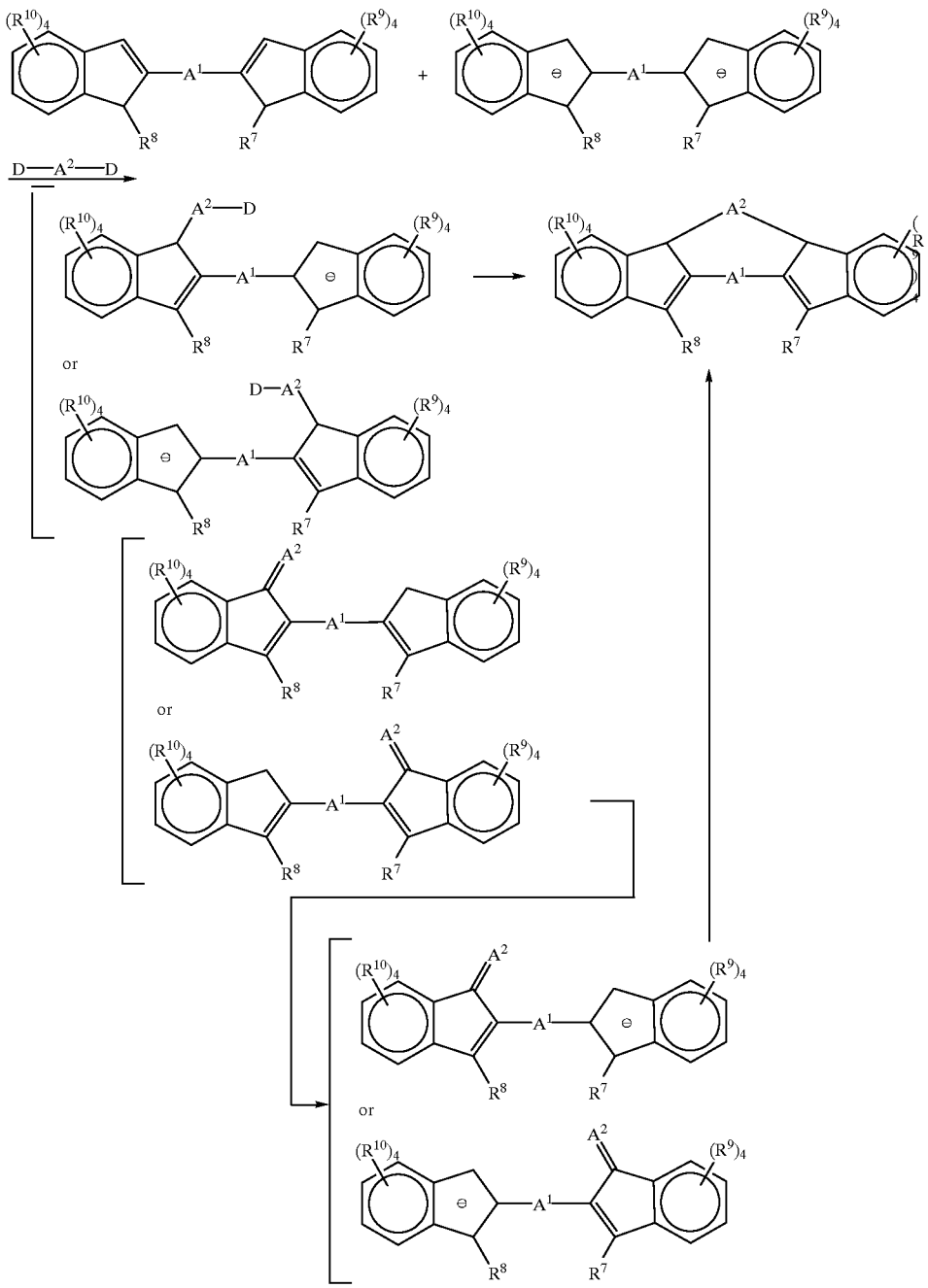

The catalyst for olefin polymerization of the present invention is a catalyst comprising (A) the transition metal compound represented by the general formula (I), an activation cocatalyst, for example, (B) a compound capable of reacting with the transition metal compound of the component (A) or its derivative to form an ionic complex, and if necessary, (C) an organic aluminum compound.

In this catalyst for polymerization, the transition metal compounds represented by the general formula (I), which can be used as the component (A), may be used singly or in a combination of two or more thereof.

In this catalyst for polymerization of the present invention, the component (A) and the activation cocatalyst are used. No particular restriction is put on the activation cocatalyst, but for example, as the component (B), there can be used a compound capable of reacting with the transition metal compound of the component (A) or its derivative to form an ionic complex.

As examples of this component (B), an ionic compound (B-1) capable of reacting with the transition metal compound of the component (A) to form an ionic complex, an aluminoxane (B-2) or a Lewis acid (B-3) are preferable, because they have a high polymerization activity and can reduce a catalyst cost.

As the component (B-1), any compound can be used, so far as it can react with the transition metal compound of the component (A) to form an ionic complex, but compounds represented by the following general formulae (IX) and (X) can be suitably used from the viewpoints of the particularly efficient formation of activation points for the polymerization and the like:

wherein $L^2$ is $M^4$, $R^{14}R^{15}M^3$, $R^{16}{}_3C$ or $R^{17}M^3$; $L^1$ is a Lewis base; $[Z]^-$ is a non-coordinating anion $[Z^1]^-$ or $[Z^2]^-$; here $[Z^1]^-$ is an anion in which a plurality of groups are bonded to an element, i.e., $[M^1G^1G^2 \ldots G^f]$ wherein $M^1$ is an element in the groups 5 to 15, preferably the groups 13 to 15 of the periodic table; $G^1$ to $G^f$ are each a hydrogen atom, a halogen atom, an alkyl group having 1 to 20 carbon atoms, a dialkylamino group having 2 to 40 carbon atoms, an alkoxy group having 1 to 20 carbon atoms, an aryl group having 6 to 20 carbon atoms, an aryloxy group having 6 to 20 carbon atoms, an alkylaryl group having 7 to 40 carbon atoms, an arylalkyl group having 7 to 40 carbon atoms, a halogen-substituted hydrocarbon group having 1 to 20 carbon atoms, an acyloxy group having 1 to 20 carbon atoms, an organic metalloid group or a hetero-atom-containing hydrocarbon group having 2 to 20 carbon atoms, and two or more of $G^1$ to $G^f$ may form a ring; f is an integer of [(a valence of the central metal $M^1$)+1]; $[Z^2]^-$ is a Brønsted acid single in which a logarithm (pKa) of a reciprocal number of an acid dissociation constant is −10 or less, a conjugated base of a combination of the Brønsted acid and a Lewis acid, or a conjugated base usually defined as a superstrong acid, and $[Z^2]^-$ may be coordinated with a Lewis base; $R^{13}$ is a hydrogen atom, an alkyl group having 1 to 20 carbon atoms, an aryl group, an alkylaryl group or an arylalkyl group having 6 to 20 carbon atoms; $R^{14}$ and $R^{15}$ are each a cyclopentadienyl group, a substituted cyclopentadienyl group, an indenyl group or a fluorenyl group; $R^{16}$ is an alkyl group, an aryl group, an alkylaryl group or an arylalkyl group having 1 to 20 carbon atoms; $R^{17}$ is a large cyclic ligand such as tetraphenylporphyrin or phthalocyanine; h is an ionic valence of $[L^1-R^{13}]$ or $[L^2]$ and it is an integer of 1 to 3; a is an integer of 1 or more; b is (hxa); $M^2$ is an element in the groups 1 to 3, 11 to 13 and 17 of the periodic table; and $M^3$ is an element in the groups 7 to 12 of the periodic table.

Here, typical examples of Ll include amines such as ammonia, methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline and p-nitro-N,N-dimethylaniline, phosphines such as triethylphosphine, triphenylphosphine and diphenylphosphine, a thioether such as tetrahydrothiophene, an ester such as ethyl benzoate, and nitrites such as acetonitrile and benzonitrile.

Typical examples of $R^{13}$ include hydrogen, a methyl group, an ethyl group, a benzyl group and a trityl group, and typical examples of $R^{14}$ and $R^{15}$ include a cyclopentadienyl group, a methylcyclopentadienyl group, an ethylcyclopentadienyl group and a pentamethylcyclopentadienyl group. Typical examples of $R^{16}$ include a phenyl group, a p-tolyl group and a p-methoxyphenyl group, and typical examples of $R^{17}$ include tetraphenylporphine, phthalocyanine, allyl and methallyl. Typical examples of $M^2$ include Li, Na, K, Ag, Cu, Br, I and $I_3$, and typical examples of $M^3$ include Mn, Fe, Co, Ni or Zn.

Furthermore, typical examples of $M^1$ in $[Z^1]^-$, i.e., $[M^1G^1G^2 \ldots G^f]$ include B, Al, Si, P, As and Sb, and above all, B and Al are preferable. Typical examples of $G^1$, $G^2$ to $G^f$ include dialkylamino groups such as a dimethylamino group and a diethylamino group, alkoxy groups and aryloxy groups such as a methoxy group, an ethoxy group, an n-butoxy group and a phenoxy group, hydrocarbon groups such as a methyl group, an ethyl group, an n-propyl group, an isopropyl group, an n-butyl group, an isobutyl group, an n-octyl group, an n-eicosyl group, a phenyl group, a p-tolyl group, a benzyl group, a 4-t-butylphenyl group and a 3,5-dimethylphenyl group, halogen atoms such as fluorine, chlorine, bromine and iodine, hetero-atom-containing hydrocarbon groups such as a p-fluorophenyl group, a 3,5-difluorophenyl group, a pentachlorophenyl group, a 3,4,5-trifluorophenyl group, a pentafluorophenyl group, a 3,5-bis(trifluoromethyl)phenyl group and a bis(trimethylsilyl)methyl group, and organic metalloid groups such as a pentamethylantimony group, a trimethylsilyl group, a trimethylgermyl group, a diphenylarsine group, a dicyclohexylantimony group and a diphenylboron group.

Typical examples of the non-coordinating anion, i.e., the conjugated base $[Z^2]^-$ which is the Brønsted acid single having a pKa of −10 or less or the combination of the Brønsted acid and the Lewis acid include trifluoromethanesulfonic acid anion $(CF_3SO_3)^-$, bis(trifluoromethanesulfonyl)methyl anion, bis(trifluoromethanesulfonyl)benzyl anion, bis(trifluoromethanesulfonyl)amide, perchloric acid anion $(ClO_4)^-$, trifluoroacetic acid anion $(CF_3CO_2)^-$, hexafluoroantimony anion $(SbF_6)^-$, fluorosulfonic acid anion $(FSO_3)^-$, chlorosulfonic acid anion $(ClSO_3)^-$, fluorosulfonic acid anion-5-antimony fluoride $(FSO_3—SbF_5)^-$, fluorosulfonic acid anion-5-arsenic fluoride $(FSO_3—AsF_5)^-$ and trifluoromethanesulfonic acid-5-antimony fluoride $(CF_3SO_3—SbF_5)^-$.

Typical examples of the ionic compound, i.e., the (B-1) component compound capable of reacting with the transition metal compound of the above-mentioned component (A) to form an ionic complex include triethylammonium tetraphenylborate, tri-n-butylammonium tetraphenylborate, trimethylammonium tetraphenylborate, tetraethylammonium tetraphenylborate, methyl (tri-n-butyl) ammonium tetraphenylborate, benzyl(tri-n-butyl)ammonium tetraphenylborate, dimethyldiphenylammonium tetraphenylborate, triphenyl(methyl)ammonium tetraphenylborate, trimethylanilinium tetraphenylborate, methylpyridinium tetraphenylborate, benzylpyridinium tetraphenylborate, methyl(2-cyanopyridinium) tetraphenylborate, triethylammonium tetrakis(pentafluorophenyl)borate, tri-n-butylammonium tetrakis(pentafluorophenyl)borate, triphenylammonium tetrakis(pentafluorophenyl)borate, tetra-n-butylammonium tetrakis(pentafluorophenyl)borate, tetraethylammonium tetrakis(pentafluorophenyl)borate, benzyl(tri-n-butyl)ammonium tetrakis(pentafluorophenyl)borate, methyldiphenylammonium tetrakis(pentafluorophenyl)borate, triphenyl(methyl) ammonium tetrakis(pentafluorophenyl)borate, methylanilinium tetrakis(pentafluorophenyl)borate, dimethylanilinium tetrakis(pentafluorophenyl)borate, trimethylanilinium tetrakis(pentafluorophenyl)borate, methylpyridinium tetrakis(pentafluorophenyl)borate, benzylpyridinium tetrakis(pentafluorophenyl)borate, methyl(2-cyanopyridinium) tetrakis(pentafluorophenyl)borate, benzyl (2-cyanopyridinium) tetrakis(pentafluorophenyl)borate, methyl(4-cyanopyridinium) tetrakis(pentafluorophenyl) borate, triphenylphosphonium tetrakis(pentafluorophenyl) borate, dimethylanilinium tetrakis[bis(3,5-ditrifluoromethyl)-phenyl]borate, ferrocenium tetraphenylborate, silver tetraphenylborate, trityl tetraphenylborate, tetraphenylporphyrinmanganese tetraphenylborate, ferrocenium tetrakis(pentafluorophenyl) borate, (1,1'-dimethylferrocenium) tetrakis (pentafluorophenyl)borate, decamethylferrocenium tetrakis (pentafluorophenyl)borate, silver tetrakis (pentafluorophenyl)borate, trityl tetrakis(pentafluorophenyl) borate, lithium tetrakis(pentafluorophenyl)borate, sodium tetrakis(pentafluorophenyl)borate, tetraphenylporphyrin-manganese tetrakis(pentafluorophenyl)borate, silver tetrafluoroborate, silver hexafluorophosphate, silver hexafluoroarsenate, silver perchlorate, silver trifluoroacetate and silver trifluoromethanesulfonate.

The ionic compounds, which can be used as the component (B-1), capable of reacting with the transition metal compound of the component (A) to form an ionic complex may be used singly or in a combination of two or more thereof.

On the other hand, examples of the aluminoxane which is the component (B-2) include a chain aluminoxane represented by the general formula (XI)

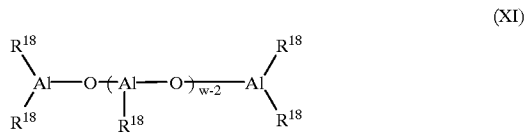

(XI)

wherein $R^{18}$ is a hydrocarbon group such as an alkyl group, an alkenyl group, an aryl group or an arylalkyl group having 1 to 20 carbon atoms, preferably 1 to 12 carbon atoms or a halogen atom, and a plurality of $R^{18}$s may be the same or different; and w is an average polymerization degree and it is usually an integer of 2 to 50, preferably 2 to 40, and a cyclic aluminoxane represented by the general formula (XII)

(XII)

wherein $R^{18}$ and w are the same as in the above-mentioned general formula (XI).

A method for preparing the above-mentioned aluminoxane comprises the step of bringing an alkylaluminum into contact with a condensing agent such as water, but its means is not particularly limited and a known procedure can be used to carry out a reaction. For example, there are (1) a method which comprises dissolving an organic aluminum compound in an organic solvent, and then bringing the solution into contact with water, (2) a method which comprises first adding an organic aluminum compound to a polymerization system at the time of polymerization, and then adding water, (3) a method which comprises reacting an organic aluminum compound with crystal water contained in a metallic salt or water adsorbed on an inorganic material or an organic material, and (4) a method which comprises reacting a tetraalkyldialuminoxane with trialkylaluminum, and then reacting the resultant reaction product with water. In this connection, the aluminoxane which is insoluble in toluene is also usable.

These aluminoxanes may be used singly or in a combination of two or more thereof.

No particular restriction is put on the Lewis acid which is the component (B-3), and it may be an organic compound or a solid inorganic compound. As the organic compound, a boron compound or an aluminum compound can preferably be used, and as the inorganic compound, a magnesium compound or an aluminum compound can preferably be used, because they can efficiently form activation points. Examples of the aluminum compound as the organic compound include bis(2,6-di-t-butyl-4-methylphenoxy) aluminummethyl and (1,1-bi-2-naphthoxy) aluminummethyl, and examples of the magnesium compound include magnesium chloride and diethoxymagnesium. Examples of the aluminum compound as the inorganic compound include aluminum oxide and aluminum chloride, and examples of the boron compound include triphenylboron, tris(pentafluorophenyl)boron, tris[3,5-bis (trifluoromethyl)phenyl]boron, tris[(4-fluoromethyl)phenyl] boron, trimethylboron, triethylboron, tri-n-butylboron, tris (fluoromethyl)boron, tris(pentafluoroethyl)boron, tris (nonafluorobutyl)boron, tris(2,4,6-trifluorophenyl)boron, tris(3,5-difluoro)boron, tris[3,5-bis(trifluoromethyl)phenyl] boron, bis(pentafluorophenyl)fluoroboron, diphenylfluoroboron, bis(pentafluorophenyl)chloroboron, dimethylfluoroboron, diethylfluoroboron, di-n-butylfluoroboron, pentafluorophenyldifluoroboron, phenyldifluoroboron, pentafluorophenyldichloroboron, methyldifloroboron, ethyldifluoroboron and n-butyldifluoroboron.

These Lewis acids may be used singly or in a combination of two or more thereof.

A molar ratio of the catalytic component (A) to the catalytic component (B) in the catalyst for polymerization of the present invention is preferably in the range of 10:1 to 1:100, more preferably 2:1 to 1:10 in the case that the compound (B-1) is used as the catalytic component (B), and if the molar ratio deviates from the above-mentioned range, the catalyst cost per unit weight of an obtained polymer increases, which is not practical. In the case that the compound (B-2) is used, the molar ratio is preferably in the range of 1:1 to 1:1000000, more preferably 1:10 to 1:10000. If the molar ratio deviates from the above-mentioned range, the catalyst cost per unit weight of an obtained polymer increases, which is not practical.

A molar ratio of the catalytic component (A) to the catalytic component (B-3) is preferably in the range of 10:1 to 1:2000, more preferably 5:1 to 1:1000, most preferably 2:1 to 1:500, and if the molar ratio deviates from the above-mentioned range, the catalyst cost per unit weight of an obtained polymer increases, which is not practical. Furthermore, as the catalytic component (B), the compounds (B-1), (B-2) and (B-3) may be used singly or in a combination of two or more thereof.

The catalyst for polymerization of the present invention may contain the above-mentioned components (A) and (B) as the main components, or alternatively, it may contain the components (A) and (B) as well as an organic aluminum compound (C) as the main components.

Here, as the organic aluminum compound of the component (C), there can be used a compound represented by the general formula (XIII)

$R^{19}{}_v AlQ_{3-v}$ (XIII)

wherein $R^{19}$ is an alkyl group having 1 to 10 carbon atoms; Q is a hydrogen atom, an alkoxy group having 1 to 20 carbon atoms, an aryl group having 6 to 20 carbon atoms or a halogen atom; and v is an integer of 1 to 3.

Typical examples of the compound represented by the general formula (XIII) include trimethylaluminum, triethylaluminum, triisopropylaluminum, triisobutylaluminum, dimethylaluminum chloride, diethylaluminum chloride, methylaluminum dichloride, ethylaluminum dichloride, dimethylaluminum fluoride, diisoblutylaluminum hydride, diethylaluminum hydride and ethylaluminum sesquichloride.

These organic aluminum compounds may be used singly or in a combination of two or more thereof.

A molar ratio of the catalytic component (A) to the catalytic component (C) is preferably in the range of 1:1 to 1:10000, more preferably 1:5 to 1:2000, most preferably 1:10 to 1:1000. The employment of the catalytic component (C) enables a polymerization activity per transition metal to improve, but if the amount of the catalytic component (C) is excessively large, particularly if it is in excess of the above-mentioned range, the organic aluminum compound is used in vain and it remains in large quantities in the polymer. Conversely, if it the amount of the catalytic component (C) is small, a sufficient catalytic activity cannot be obtained unpreferably sometimes.

In the present invention, at least one of the catalytic components, when used, may be supported on a suitable carrier. No particular restriction is put on the kind of carrier, and any of an inorganic oxide carrier, another inorganic carrier and an organic carrier can be used, but the inorganic oxide carrier or the other inorganic carrier is particularly preferable from the viewpoint of morphology control.

Typical examples of the inorganic oxide carrier include $SiO_2$, $Al_2O_3$, MgO, $ZrO_2$, $TiO_2$, $Fe_2O_3$, $B_2O_3$, CaO, ZnO, BaO, $ThO_2$ and mixtures thereof such as silica-alumina, zeolites, ferrites and glass fibers. Above all, $SiO_2$ and $Al_2O_3$ are particularly preferable. The above-mentioned inorganic oxide carrier may contain a small amount of a carbonate, a nitrate, a sulfate or the like.

On the other hand, examples of usable carriers other than mentioned above include magnesium compounds represented by the general formula $MgR^{20}{}_xX^2{}_y$ typified by magnesium compounds such as $MgCl_2$ and $Mg(OC_2H_5)_2$, and complexes thereof. In this general formula, $R^{20}$ is an alkyl group having 1 to 20 carbon atoms, an alkoxy group having 1 to 20 carbon atoms or an aryl group having 6 to 20 carbon atoms; $X^2$ is a halogen atom or an alkyl group having 1 to 20 carbon atoms; x is 0 to 2; and y is 0 to 2, and x+y=2. A plurality of $R^{20}$s and $X^2$s may be the same or different.

Examples of the organic carrier include polymers such as polystyrenes, styrene-divinylbenzene copolymers, polyethylenes, polypropylenes, substituted polystyrenes and polyacrylates, starch and carbon.

Preferable examples of the carrier which can be used in the present invention include $MgCl_2$, $MgCl(OC_2H_5)$, $Mg(OC_2H_5)_2$, $SiO_2$ and $Al_2O_3$. The characteristics of the carrier depend upon its kind and preparation method, but the average particle diameter of the carrier is usually in the range of 1 to 300 μm, preferably 10 to 200 μm, more preferably 20 to 100 μm.

If the particle diameter is small, the amount of a fine powder in the polymer increases, and if it is large, the amount of the coarse particles increase in the polymer, which leads to the deterioration of bulk density and the clogging of a hopper.

The specific surface area of the carrier is usually in the range of 1 to 1000 $m^2/g$, preferably 50 to 500 $m^2/g$, and the pore volume of the carrier is usually in the range of 0.1 to 5 $cm^3/g$, preferably 0.3 to 3 $cm^3/g$.

If either of the specific surface area or the pore volume deviates from the above-mentioned range, the catalytic activity deteriorates on occasion. The specific surface area or the pore volume can be determined on the basis of the volume of a nitrogen gas adsorbed, for example, by a BET method [J. Am. Chem. Soc., Vol. 60, p. 309 (1983)].

Furthermore, the carrier is suitably calcined usually at 150 to 1000° C., preferably 200 to 800° C. prior to its use.

In the case that at least one of the catalytic components is supported on the above-mentioned carrier, at least one of the catalytic components (A) and (B), preferably both of the catalytic components (A) and (B) are supported, which is desirable from the viewpoints of morphology control and applicability to a process such as gaseous phase polymerization.

No particular restriction is put on a method for supporting at least one of the catalytic components (A) and (B) on the carrier, but there can be used, for example, (1) a method which comprises mixing at least one of the catalytic components (A) and (B) with the carrier, (2) a method which comprises first treating the carrier with an organic aluminum compound or a halogen-containing silicon compound, and then mixing at least one of the catalytic components (A) and (B) with the treated carrier in an inert solvent, (3) a method which comprises reacting the carrier, one or both of the catalytic components (A) and (B) and an organic aluminum compound or a halogen-containing silicon compound, (4) a method which comprises supporting the component (A) or the component (B) on the carrier, and then mixing the carrier with the component (B) or the component (A), (5) a method which comprises mixing the carrier with a catalytic reaction product of the component (A) and the component (B), or (6) a method which comprises carrying out a catalytic reaction of the component (A) and the component (B) in the presence of the carrier.

In the reaction of the above-mentioned methods (4), (5) and (6), the organic aluminum compound which is the component (C) can be added.

The thus obtained catalyst may be used for the polymerization after it has been taken out as a solid by distilling off a solvent, or it may be used as it is without isolation.

In the present invention, the catalyst can be prepared by carrying out an operation of supporting at least one of the component (A) and the component (B) on the carrier in a polymerization system. For example, a method can be employed which comprises adding at least one of the components (A) and (B), the carrier and if necessary, the organic aluminum compound as the above-mentioned component (C) to the system, further adding an olefin such as ethylene as much as a pressure of from atmospheric pressure to 20 $kg/cm^2$, and then carrying out prepolymerization at −20 to 200° C. for a period of 1 minute to 2 hours to form catalyst particles.

In the present invention, a weight ratio of the compound component (B-1) to the carrier is preferably in the range of 1:5 to 1:10000, more preferably 1:10 to 1:500; a weight ratio of the compound component (B-2) to the carrier is preferably in the range of 1:0.5 to 1:1000, more preferably 1:1 to 1:50; and a weight ratio of the compound component (B-3) to the carrier is preferably in the range of 1:5 to 1:10000, more preferably 1:10 to 1:500. In the case that two or more kinds of catalytic components (B) is used in the form of a mixture, the weight ratios of these components (B) to the carrier are desirably within the above-mentioned ranges, respectively. A weight ratio of the component (A) to the carrier is preferably 1:5 to 1:10000, more preferably 1:10 to 1:500.

If the use ratio of the component (B) [the component (B-1), the component (B-2) or the component (B-3)] to the carrier, or the use ratio of the component (A) to the carrier deviates from the above-mentioned range, the activity deteriorates on occasion. The average particle diameter of the thus prepared catalyst for polymerization according to the present invention is usually in the range of 2 to 200 mm, preferably 10 to 150 mm, more preferably 20 to 100 mm, and the specific surface area of the catalyst is usually in the range of 20 to 1000 m$^2$/g, preferably 50 to 500 m$^2$/g. If the average particle diameter of the catalyst is less than 2 mm, the amount of a fine powder in the polymer increases sometimes, and if it is more than 200 mm, the amount of the coarse particles increase in the polymer sometimes. If the specific surface area of the catalyst is less than 20 m$^2$/g, the activity deteriorates on occasion, and it is more than 1000 m$^2$/g, the bulk density of the polymer deteriorates sometimes. Furthermore, in the catalyst of the present invention, the amount of the transition metal in 100 g of the carrier is usually in the range of 0.05 to 10 g, preferably 0.1 to 2 g. If the amount of the transition metal deviates from the above-mentioned range, the activity deteriorates on occasion.

This technique of supporting the components on the carrier enables the formation of the industrially advantageous polymer having the high bulk density and an excellent particle diameter distribution.

The catalyst for olefin polymerization of the present invention is particularly excellent in copolymerizability, and so it can suitably be used in the manufacture of a linear low-density polyethylene. Furthermore, the transition metal compound of the catalytic component (A) can suitably be selected and used in order to prepare an isotactic polypropylene or an atactic polypropylene.

According to the preparation method of the olefin polymer regarding the present invention, the homopolymerization of an olefin or the copolymerization of an olefin and another olefin and/or another monomer (i.e., the copolymerization of different kinds of olefins, the copolymerization of an olefin and another monomer, or the copolymer of different kinds of olefins and another monomer) can be suitably carried out by the use of the above-mentioned catalyst for polymerization.

No particular restriction is put on the kind of olefins, but α-olefins having 2 to 20 carbon atoms are preferable. Examples of the α-olefins include ethylene, propylene, 1-butene, 3-methyl-1-butene, 1-pentene, 1-hexene, 4-methyl-1-pentene, 1-octene, 1-decene, 1-dodecene, 1-tetradecene, 1-hexadecene, 1-octadecene, 1-eicosene, styrene, p-methylstyrene, isopropylstyrene and t-butylstyrene. The above-mentioned other olefin can also suitably be selected from these olefins mentioned above.

In the present invention, the above-mentioned olefins may be used singly or in a combination of two or more thereof. In the case that two or more olefins are copolymerized, these olefins can optionally be combined. At this time, for example, when propylene is copolymerized with ethylene or ethylene is copolymerized with an α-olefin having 3 to 10 carbon atoms, a copolymerization ratio (molar ratio) of propylene and ethylene, or ethylene and the α-olefin having 3 to 10 carbon atoms is usually selected in the range of 99.9:0.1 to 0.1 to 99.9, preferably 99.5:0.5 to 75.0:25.0.

In the present invention, the above-mentioned olefin may be copolymerized with another monomer, and examples of the other monomer which can be used at this time include chain diolefins such as butadiene, isoprene and 1,5-hexadiene, cyclic olefins such as norbornene, 1,4,5,8-dimethanol-1,2,3,4,4a,5,8,8a-octahydronaphthalene and 2-norbornene, cyclic diolefins such as norbornadiene, 5-ethylidenenorbornene, 5-vinylnorbornene and dicyclopentadiene, unsaturated esters such as ethyl acrylate and methyl methacrylate, lactones such as β-propiolactone, β-butyrolactone and γ-butyrolactone, lactams such as ε-caprolactam and δ-valerolactam, and epoxides such as epoxypropane and 1,2-epoxybutane.

Incidentally, the catalyst for polymerization of the present invention can be used not only for the polymerization of the above-mentioned olefin but also for the polymerization of a monomer other than the olefin.

In the present invention, no particular restriction is put on a polymerization method, and any of a slurry polymerization method, a gaseous phase polymerization method, a bulk polymerization method, a solution polymerization method and a suspension polymerization method can be used, but the slurry polymerization method and the gaseous phase polymerization method are preferable from the viewpoints of a high productivity and less process steps.

With regard to the conditions of the polymerization, a polymerization temperature is usually in the range of −100 to 250° C., preferably −50 to 200° C., more preferably 0 to 130° C. Furthermore, a use ratio of the catalyst to the reaction material is such that the material monomer/the above-mentioned component (A) (molar ratio) is preferably in the range of 1 to $10^8$, more preferably 100 to $10^5$. Moreover, a polymerization time is usually in the range of 5 minutes to 10 hours, and a reaction pressure is preferably in the range of from atmospheric pressure to 200 kg/cm$^2$G, more preferably from atmospheric pressure to 100 kg/cm$^2$G.

The molecular weight of the polymer can be adjusted by selecting the kinds and the amounts of catalytic components and the polymerization temperature, and by carrying out the polymerization in the presence or absence of hydrogen.

In the case that a polymerization solvent is employed, examples of the usable solvent include aromatic hydrocarbons such as benzene, toluene, xylene and ethylbenzene, alicyclic hydrocarbons such as cyclopentane, cyclohexane and methylcyclohexane, aliphatic hydrocarbons such as pentane, hexane, heptane and octane, and halogenated hydrocarbons such as chloroform and dichloromethane. These solvents may be used singly or in a combination of two or more thereof. In addition, a monomer such as an α-olefin may be used as the solvent. In a certain polymerization method, the polymerization can be carried out in the absence of any solvent.

No particular restriction is put on the molecular weight of the polymer which can be obtained by such a process, but its intrinsic viscosity [η] (measured in decalin at 135° C.) is preferably 0.1 dl/g or more, more preferably 0.2 dl/g or more. If the intrinsic viscosity is less than 0.1 dl/g, sufficient mechanical properties cannot be obtained, and hence the polymer having such a low intrinsic viscosity is not practical.

In the present invention, prepolymerization can be carried out by the use of the above-mentioned catalyst for polymerization. The prepolymerization can be accomplished by bringing a small amount of an olefin into contact with the solid catalytic component, but its procedure is not particularly limited and a known method can be used. No particular restriction is put on the olefin for use in the prepolymerization, and such olefins as mentioned above, for example, ethylene, α-olefins having 3 to 20 carbon atoms and mixtures thereof are usable, but it is advantageous to employ the same olefin as used in the polymerization.

A prepolymerization temperature is usually in the range of −20 to 200° C., preferably −10 to 130° C., more preferably 0 to 80° C. In the prepolymerization, an inactive hydrocarbon, an aliphatic hydrocarbon, an aromatic hydrocarbon or a monomer can be used as the solvent. Above all, the aliphatic hydrocarbon is particularly preferable. The prepolymerization may be carried out in the absence of any solvent.

In the prepolymerization, conditions are desirably regulated so that the intrinsic viscosity [η] (measured in decalin at 135° C.) of a prepolymerized product may be 0.2 dl/g or more, preferably 0.5 dl/g or more and so that the amount of the prepolymerized product per mmol of the transition metal component in the catalyst may be in the range of 1 to 10,000 g, preferably 10 to 1,000 g.

Thus, an olefin polymer of the present invention having a uniform composition and a narrow molecular weight distribution can efficiently be obtained.

Furthermore, with regard to a conventional crosslinking type metallocene catalyst, if hydrogen is added thereto as a molecular weight modifier, there is a tendency that the activity of the catalyst deteriorates with the increase of its amount. On the contrary, with regard to the catalyst of the present invention, the catalyst activity can unexpectedly enhance with the increase of its amount. In the present invention, therefore, the molecular weight of the olefin polymer can easily be adjusted by adding hydrogen to a reaction system during the polymerization.

Next, the present invention will be described in more detail with reference to examples, but the scope of the present invention should not be limited at all by these examples.

EXAMPLE 1

(1) Preparation of ethyl(2-indenyl) acetate

Under a nitrogen gas stream, 3.3 g (0.14 mol) of sodium hydride was suspended in 300 ml of tetrahydrofuran, and the suspension was then cooled to 10° C. To the cooled suspension, 200 ml of a tetrahydrofuran solution containing 28.3 g (0.11 mol) of ethyldiethyl phosphonoacetate was added dropwise over 1 hour. After the dropping, the suspension was stirred at room temperature for 30 minutes, and then ice-cooled. Next, 75 ml of a tetrahydrofuran solution containing 16.33 g (0.12 mol) of 2-indanone was added thereto dropwise over 1 hour. After the dropping, the solution was stirred at room temperature for 30 minutes, and hydrolysis was carried out with water. Extraction was done with 500 ml of diethyl ether, and after the separation of the resultant organic layer, the solvent was distilled off under reduced pressure. The resultant residue was subjected to vacuum distillation, thereby isolating ethyl(2-indenyl) acetate in the state of a light yellow oil. Its yield was 11.06 g, i.e., 49.5%.

The $^1$H-NMR of this product was measured, and the following results were obtained.

$^1$H-NMR (CDCl$_3$): 1.23 (t, 3H), 3.40 (s, 2H), 3.45 (s, 2H), 4.16 (q, 2H), 6.65 (s, 1H), 6.94–7.50 (m, 4H)

(2) Preparation of 2-(2-indenyl)-ethanol

Under a nitrogen gas stream, 2.2 g (58.49 mmol) of lithiumaluminum hydride was suspended in 100 ml of diethyl ether. To this suspension, 50 ml of a diethyl ether solution containing 11 g (59.06 mmol) of ethyl(2-indenyl) acetate obtained in the above-mentioned (1) was added dropwise over 1 hour. After the dropping, the solution was stirred at room temperature for 30 minutes and then ice-cooled, and 50 ml of water was slowly added and dilute hydrochloric acid was further added thereto so as to dissolve impurities. The resultant organic layer was separated, and the solvent was then distilled off under reduced pressure to obtain 2-(2-indenyl)-ethanol in the state of a white solid. Its yield was 7.89 g.

The thus obtained product was used in the next reaction without further purification. The $^1$H-NMR of this product was measured, and the following results were obtained.

$^1$H-NMR (CDCl$_3$): 1.56 (s, 1H), 2.76 (t, 2H), 3.37 (s, 2H), 3.83 (t, 2H), 6.62 (s, 1H), 6.95–7.62 (m, 4H)

(3) Preparation of 1-bromo-2-(2-indenyl)ethane

Under a nitrogen gas stream, 4.61 g (28.77 mmol) of 2-(2-indenyl)-ethanol obtained in the above-mentioned (2) was dissolved in 65 ml of dichloromethane. To this solution, 7.66 g (29.20 mmol) of triphenylphosphine was added, and afterward, 5.19 g (29.16 mol) of N-bromo-succinimide was slowly added. After the addition of N-bromosuccinimide, the solution was stirred at room temperature for 30 minutes, and water was added thereto, followed by stirring. Next, the resultant organic layer was separated and then dried over magnesium sulfate, and the solvent was distilled off under reduced pressure. The residue was purified through a silica gel column (developing solvent: hexane) to obtain 1-bromo-2-(2-indenyl)ethane in the state of a colorless oil. Its yield was 5.07 g, i.e., 80.85%.

The $^1$H-NMR of this product was measured, and the following results were obtained.

$^1$H-NMR (CDCl$_3$): 3.20 (t, 2H), 3.32 (s, 2H), 3.52 (t, 2H), 6.60 (s, 1H), 6.93–7.53 (m, 4H)

(4) Preparation of (1,2'-ethylene)(2,1'-ethylene)-bis(indene)

Under a nitrogen gas stream, 6.87 ml (52.41 mmol) of diisopropylamine was added to 50 ml of tetrahydrofuran, and the mixture was then cooled to −78° C. To this solution, 31.96 ml (n-butyllithium: 52.41 mmol) of a hexane solution having an n-butyllithium concentration of 1.64 mol/l was added dropwise over 10 minutes. After the dropping, the temperature of the reaction mixture was allowed to spontaneously rise, thereby preparing an LDA (lithium diisopropylamide) solution.

Next, under a nitrogen gas stream, 11.69 g (52.39 mmol) of 1-bromo-2-(2-indenyl)ethane obtained in the above-mentioned (3) was added to 500 ml of tetrahydrofuran, and after stirring and dissolution, the solution was cooled to −78° C. Next, the previously prepared LDA solution which was cooled to −78° C. was added dropwise to this solution over 30 minutes. After the dropping of the LDA solution, the temperature of the solution was allowed to spontaneously rise to room temperature, followed by stirring for 12 hours. To this reaction mixture, 500 ml of water was added, and after the washing of the resulting organic layer, anhydrous magnesium sulfate was added thereto in order to dry the organic layer. After magnesium sulfate was removed by filtration, the solvent was distilled off under reduced pressure to obtain 5.95 g of a crude product of (1,2'-ethylene)(2,1'-ethylene)-bis(indene) in the state of a white solid. This crude product was analyzed by an FD-MS (field desorption-mass spectrum) method, and as a result, intended (1,2'-ethylene)(-2,1'-ethylene)-bis(indene) (dimer) was confirmed. Next, this crude product was purified by sublimation at 150° C. under 0.2 Torr to obtain 1.87 g of (1,2'-ethylene)(2,1'-ethylene)-bis(indene). Its yield was 25.1%.

The structure of this product was confirmed by FD-MS and $^1$H-NMR. In this case, the measurement of FD-MS was carried out under an accelerating voltage of 8 kV.

$^1$H-NMR (CDCl$_3$): 3.20 (s, 8H), 3.29 (s, 4H), 7.0–7.5 (m, 8H); FD-MS: M$^+$=284.

(5) Preparation of dilithium salt of (1,2'-ethylene)(2,1'-ethylene)-bis(indene)

Under a nitrogen gas stream, 100 ml of diethyl ether was added to 1.87 g (6.58 mmol) of (1,2'-ethylene)(2,1'-ethylene)-bis(indene) obtained in the above-mentioned (4), and the mixture was stirred and then cooled to −78° C. To the cooled mixture, 8.02 ml (n-butyllithium: 13.15 mmol) of a hexane solution having an n-butyllithium concentration of 1.64 mol/l was added dropwise over 30 minutes. After the temperature of the reaction mixture was allowed to spontaneously rise to room temperature, followed by stirring at room temperature for 12 hours. Next, this reaction mixture was treated under reduced pressure to distill off the solvent, and the resulting residue was then washed twice with 50 ml of hexane. Drying was carried out under reduced pressure to obtain dilithium salt of (1,2'-ethylene)(2,1'-ethylene)-bis (indene) in the state of a light yellow powder. According to $^1$H-NMR, this product was a diethyl ether adduct and afterward used in the next reaction. Its yield was 1.63 g, i.e., 69.3%.

$^1$H-NMR (THF-d$_8$): 3.22 (8H), 5.38 (s, 2H), 5.95–6.35 (m, 4H), 6.70–7.20 (m, 4H);

In this connection, THF means tetrahydrofuran.

(6) Preparation of (1,2'-ethylene)(2,1'-ethylene)-bis (indenyl)zirconium dichloride Under a nitrogen gas stream, 1.63 g (4.56 mmol) of dilithium salt of (1,2'-ethylene)(2,1'-ethylene)-bis-(indene) was suspended in 50 ml of toluene, and the suspension was then cooled to −78° C. On the other hand, under a nitrogen gas stream, 1.06 g (4.56 mmol) of zirconium tetrachloride was suspended in 100 ml of toluene, and the mixture was then cooled to −78° C. To this zirconium tetrachloride toluene suspension, the previously prepared toluene suspension of (1,2'-ethylene)(2,1'-ethylene)-bis(indene) dilithium salt was added dropwise over 30 minutes. The temperature of this reaction mixture was allowed to spontaneously rise to room temperature, followed by stirring at room temperature for 12 hours. After a toluene supernatant was removed by filtration, the residue was extracted twice with 50 ml of dichloromethane.

After the solvent was distilled off under reduced pressure, the residue was recrystallized from dichloromethane-hexane to obtain 0.25 g of (1,2'-ethylene)(2,1'-ethylene)-bis (indenyl)zirconium dichloride. Its yield was 12.3%.

According to $^1$H-NMR, the following results were obtained.

$^1$H-NMR (CDCl$_3$): 3.62 (8H), 6.53 (s, 2H), 6.90–7.60 (m, 8H).

The structure of this transition metal compound is as follows:

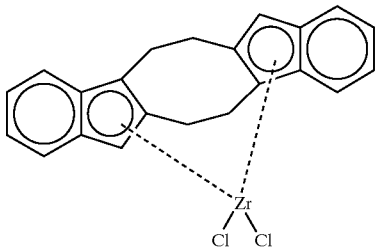

EXAMPLE 2

In a 1-liter autoclave heated and dried were placed 400 ml of toluene and 2 mmol of methylaluminoxane under a nitrogen gas stream at room temperature. After the temperature of this mixture was then raised up to 50° C., 2 micromol of (1,2'-ethylene)(2,1'-ethylene)-bis(indenyl)zirconium dichloride obtained in Example 1-(6) was added thereto, and polymerization was then carried out for 1 hour under pressure raised up to 7 kg/cm$^2$ with propylene. After the completion of the polymerization, the reaction product was poured into methanol, and the obtained polymer was collected by filtration and then washed with methanol. After the washing, the polymer was dried by heating under reduced pressure to obtain 11.33 g of a polypropylene.

This polypropylene had a pentad mesofraction [mmmm] of 85.5%, a melting point [Tm] of 135.7° C., an intrinsic viscosity [η] of 0.59 dl/g, a weight-average molecular weight Mw of 32,600, and a molecular weight distribution Mw/Mn (weight-average molecular weight/number-average molecular weight) of 2.11.

In this case, the pentad mesofraction [mmmm] was measured as a ratio of a signal at 21.8 ppm attributable to a pentad mesomoiety of the total area of 9 signals which appeared between 19 ppm and 22 ppm of $^{13}$C-NMR of the polymer.

Furthermore, the melting point was measured under conditions of device: DSC of 7 series made by Perkin Elmer Co., Ltd., temperature rise velocity: 10° C./min temperature range: −50 to 150° C., and the intrinsic viscosity [η] was measured at 135° C. in decalin.

Furthermore, the molecular weight and the molecular weight distribution were measured in terms of polystyrene under conditions of device: Waters ALC/GPC150C column: TSK HM +GMH6×2, made by Tosoh solvent: 1,2,4-trichlorobenzene temperature: 135° C.

flow rate: 1 ml/min by a gel permeation chromatography (GPC) method.

EXAMPLE 3

In a 1-liter autoclave heated and dried were placed 380 ml of toluene, 20 ml of 1-octene and 1 mmol of triisobutylaluminum under a nitrogen atmosphere at room temperature. After the temperature of the solution was raised up to 60° C. with stirring, 0.5 micromol of (1,2'-ethylene)(2,1'-ethylene)-bis(indenyl)zirconium dichloride obtained in Example 1-(6) and 2 micromol of N,N'-dimethyl-anilinium tetrakis (pentafluorophenyl)borate were added thereto at 60° C., followed by heating the solution up to 80° C. Next, ethylene was continuously introduced thereinto at 80° C. to carry out polymerization for 10 minutes, while 8 atm was maintained. After the completion of the reaction, the reaction product was poured into a methanolhydrochloric acid solution, and the mixture was then sufficiently stirred. The reaction product was collected by filtration, sufficiently washed with methanol, and then dried to obtain 53.6 g of a polymer.

This polymer had an intrinsic viscosity [η] of 2.12 dl/g, a melting point of 110.3° C., a 1-octene unit content of 2.7 mol %, a melting energy (ΔH) of 121.0 J/g, and a catalyst activity of 1175 kg/g·Zr·hr.

EXAMPLE 4

The same procedure as in Example 3 was conducted except that 1 mmol of triisobutylaluminum was replaced with 1 mmol of methylaluminoxane and N,N'-dimethylanilinium tetrakis(pentafluorophenyl)borate was not used.

As a result, the yield of the polymer was 40.8 g, and the polymer had an intrinsic viscosity [η] of 1.09 dl/g, a melting point of 106.1° C., a 1-octene unit content of 3.5 mol %, a melting energy (ΔH) of 92.5 J/g, and a catalyst activity of 895 kg/g·Zr·hr.

EXAMPLE 5

(1) Preparation of (1,2'-ethylene)(2,1'-ethylene)-bis(3-methylindene)

Under a nitrogen gas stream, 1.12 g (3.94 mmol) of (1,2'-ethylene)(2,1'-ethylene)-bis(indene) was dissolved in 50 ml of dehydrated ether. The solution was cooled to −78° C., and 5.01 ml (n-butyllithium: 7.87 mmol) of a hexane solution having an n-butyllithium concentration of 1.57 mol/l was then added dropwise over 30 minutes. Afterward, the temperature of the solution was raised up to room temperature, followed by stirring for 8 hours. The ether solvent was distilled off under reduced pressure, the residue was then washed with hexane to obtain 1.12 g (3.02 mmol) of a dilithium salt as an ether adduct. This dilithium salt was dissolved in 50 ml of dehydrated tetrahydrofuran, and the solution was then cooled to −78° C. To this solution, 10 ml of a tetrahydrofuran solution containing 0.42 ml (6.74 ml) of methyl iodide was added dropwise over 20 minutes, and after the solution was heated up to room temperature, stirring was done for 8 hours. After the solvent was distilled off under reduced pressure, the residue was extracted with ethyl acetate. The extract was washed with water, and the resulting organic layer was dried over anhydrous magnesium sulfate. Next, the solution was filtered, and the filtrate was then evaporated to dryness under reduced pressure to obtain 0.87 g (2.78 mmol) of desired (1,2'-ethylene)(2,1'-ethylene)-bis(3-methylindene) in a yield of 70.5%. This product was present as a mixture of isomers having double bonds on a five-membered ring.

According to $^1$H-NMR, the following results were obtained.

$^1$H-NMR (CDCl$_3$) (δ, ppm): 0.7–1.7 (a methyl group), 2.5–3.4 (a proton on the five-membered ring), 6.8–7.5 (a proton on a benzene ring)

(2) Preparation of dilithium salt of (1,2'-ethylene)(2,1'-ethylene)-bis(3-methylindene)

Under a nitrogen gas stream, 0.87 g (2.78 mmol) of (1,2'-ethylene)(2,1'-ethylene)-bis(3-methylindene) was dissolved in 35 mmol of ether, and the solution was then cooled to −78° C. To this solution, 3.7 ml (n-butyllithium: 5.81 mmol) of a hexane solution having an n-butyllithium concentration of 1.57 mol/l was added dropwise over 30 minutes, and the temperature of the solution was then raised to room temperature, followed by stirring for 8 hours. After the solvent was distilled off under reduced pressure, the residue was washed with hexane to obtain 1.03 g (2.58 mmol) of a dilithium salt as an ether adduct in a yield of 92.8%.

According to $^1$H-NMR, the following results were obtained.

$^1$H-NMR (THF-d$_8$) (δ, ppm): 2.20 (s, 6H), 3.25 (s, 8H), 6.0–7.4 (8H)

(3) Preparation of (1,2'-ethylene)(2,1'-ethylene)-bis(3-methylindenyl)zirconium dichloride 1.03 g (2.58 mmol) of the dilithium salt of (1,2'-ethylene)(2,1'-ethylene)-bis(3-methylindene) as the ether adduct was suspended in 25 ml of toluene, and the solution was then cooled to −78° C. To this solution, a toluene (20 ml) suspension containing 0.60 g (2.58 mmol) of zirconium tetrachloride was added over 20 minutes, and the temperature of the solution was then raised up to room temperature, followed by stirring for 8 hours. Afterward, a toluene supernatant was removed by filtration, and the resulting residue was then extracted twice with 50 ml of dichloromethane. After the solvent was distilled off under reduced pressure, the residue was recrystallized from dichloromethane-hexane to obtain 0.21 g of (1,2'-ethylene)(2,1'-ethylene)-bis(3-methylindenyl)zirconium dichloride in a yield of 17.3%.

According to $^1$H-NMR, the following results were obtained.

$^1$H-NMR (CDCl$_3$): 2.48 (6H, S), 3.33–3.85 (8H), 6.9–7.6 (8H)

The structure of this transition metal compound is as follows:

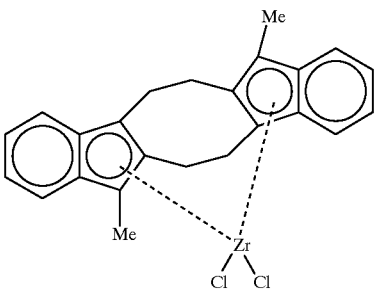

EXAMPLE 6

Polymerization was carried out in accordance with the same procedure as in Example 2 except that (1,2'-ethylene)(2,1'-ethylene)-bis(indenyl)zirconium dichloride was replaced with (1,2'-ethylene)(2,1'-ethylene)-bis(3-methylindenyl)zirconium dichloride. The yield of the obtained polypropylene was 39.15 g. This polypropylene had a pentad mesofraction [mmmm] of 58.6.%, a melting point [Tm] of 97° C., an intrinsic viscosity [η] of 0.75 dl/g, a weight-average molecular weight Mw of 45,900, and a molecular weight distribution Mw/Mn (weight-average molecular weight/number-average molecular weight) of 1.86.

EXAMPLE 7

Preparation of (1,2'-ethylene)(2,1'-ethylene)-bis(indenyl)titanium dichloride 80 ml of ether was added to 1.20 g (4.22 mmol) of (1,2'-ethylene)(2,1'-ethylene)-bis(indene), and the solution was stirred and then cooled to −78° C. To this solution, 5.80 ml (n-butyllithium: 9.28 mmol) of a hexane solution having an n-butyllithium concentration of 1.64 mol/l was added dropwise over 30 minutes, and the temperature of this reaction mixture was allowed to spontaneously rise to room temperature, followed by stirring at room temperature for 12 hours. After the resulting white precipitate was allowed to settle, and the supernatant was removed by filtration. Next, the resulting residue was washed twice with 50 ml of hexane. Drying was carried out under reduced pressure to obtain dilithium salt of (1,2'-ethylene)(2,1'-ethylene)-bis(indene) in the state of a light yellow powder. Its yield was 1.22 g, i.e., 78%.

Furthermore, 1.22 g (3.30 mmol) of this lithium salt was suspended in 50 ml of tetrahydrofuran (THF), and the suspension was then cooled to −78° C. On the other hand, under a nitrogen gas stream, 1.22 (3.30 mmol) of TiCl$_3$.(THF)$_3$ was suspended in 50 ml of tetrahydrofuran, and the suspension was then cooled to −78° C. Next, to this tetrahydrofuran suspension of TiCl$_3$.(THF)$_3$, the previously prepared tetrahydrofuran suspension of the dilithium salt of (1,2'-ethylene)(2,1'-ethylene)-bis(indene) was added dropwise over 30 minutes, and the temperature of this reaction mixture was allowed to spontaneously rise to room temperature, followed by stirring at room temperature for 12 hours. 0.94 g (6.55 mmol) of silver chloride was added to the reaction mixture, followed by stirring at room temperature for 2 hours. The reaction solution was filtered, and after the solvent was distilled off under reduced pressure, the residue was extracted twice with 50 ml of dichloromethane and the solvent was then distilled off under reduced pressure. The residue was recrystallized from dichloromethane-hexane to obtain desired (1,2'-ethylene)(2,1'-ethylene)-bis(indenyl) titanium dichloride in a green solid state. Its yield was 0.28 g, i.e., 21.2%.

According to ¹H-NMR, the following results were obtained.

¹H-NMR (CDCl₃): 3.68 (m, 8H), 6.90 (s, 2H), 7.0–7.6 (m, 8H).

The structure of this transition metal compound is as follows:

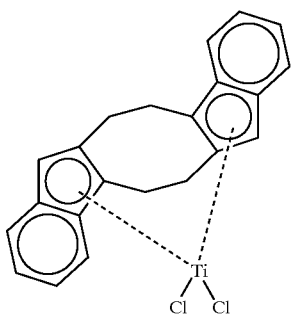

EXAMPLE 8

Preparation of (1,1'-ethylene)(2,2'-ethylene)-bis(indenyl) zirconium dichloride (1) Synthesis of 1,4-bis(phenylsulfonyl)butane In a three-necked flask were placed sodium benzenesulfinate (75.0 g, 457 mmol), tetrabutylammonium bromide (18.1 g), benzene (30 ml) and water (40 ml), and 1,4-dibromobutane (22.5 ml, 188 mmol) was further added at room temperature. After the solution was heated at 85° C. for 8 hours, its temperature was returned to room temperature, and ethyl acetate (30 ml) was added. Next, the resulting organic layer was collected, dried over anhydrous magnesium sulfate, and then concentrated under reduced pressure in an evaporator. The resulting solid was recrystallized from methanol to obtain a desired product. Its yield was 40.3 g, i.e., 63.0%.

According to ¹H-NMR, the following results were obtained.

¹H-NMR (CDCl₃): 1.79–1.82 (m, 4H), 3.05 (br t, J=6.6 Hz, 4H), 7.52–7.83 (m, 10H).

(2) Synthesis of 1,2-bis(indenyl)ethane 1,4-bis(phenylsulfonyl)butane (16.9 g, 50.0 mmol) obtained in the above-mentioned (1) was dissolved in tetrahydrofuran (500 ml). After cooling to 0° C., 128 ml (n-butyllithium: 205 mmol) of a hexane solution having an n-butyllithium concentration of 1.6 mol/l was added. After 1 hour, a tetrahydrofuran solution (500 mol) of o-xylene dichloride (17.9 g, 102 mmol) was added to the solution which was being vigorously stirred, followed by stirring at room temperature for 2 hours. Next, the solution was cooled to −78° C., and a tetrahydrofuran solution (250 ml) of lithiumdiisopropylamide prepared from a hexane solution (256 ml) having an n-butyllithium concentration of 1.6 mol/l and diisopropylamine (57.7 ml) was slowly added thereto. After 30 minutes, 5% hydrochloric acid (200 ml) was added at 0C. The solution was extracted with ethyl acetate, and the collected organic layer was dried over anhydrous magnesium sulfate. After concentration under reduced pressure, Soxhlet extraction using hexane was carried out to obtain a desired product. Its yield was 2.0 g, i.e., 15%.

According to ¹H-NMR, the following results were obtained.

¹H-NMR (CDCl₃): 2.82 (s, 4H), 3.36 (s, 4H), 6.57 (s, 2H), 7.11–7.28 (m, 8H).

(3) Synthesis of (1,1'-ethylene) (2,2'-ethylene)-bis (indene)

1,2-bis(indenyl)ethane (2.0 g, 7.8 mmol) obtained in the above-mentioned (2) was dissolved in a tetrahydrofuran solution (120 ml). After cooling to 0° C., 11.6 ml of a hexane solution (n-butyllithium: 18.6 mmol) having an n-butyllithium concentration of 1.6 mol/l was added. After 30 minutes, HMPA (3.4 ml, 15.6 mmol) was added, and after cooling to −78° C., dibromoethane (0.76 ml, 7.7 mmol) was added. After stirring at room temperature for 3 hours, water was added. Next, the organic layer was separated and then concentrated under reduced pressure by an evaporator, and the resulting solid was recrystallized from hexane-methylene chloride (3/1) to obtain (1,1'-ethylene)(2,2'-ethylene)-bis(indene). Its yield was 1.0 g, i.e., 45%.

According to ¹H-NMR, the following results were obtained.

¹H-NMR (CDCl₃): 2.97 (5, 4H), 3.05 (5, 4H), 3.27 (s, 2H), 7.0–7.4 (m, 8H)

(4) Synthesis of (1,1'-ethylene)(2,2'-ethylene)-bis (indenyl)zirconium dichloride (1,1'-ethylene)(2,2'-ethylene)-bis(indene) (1.0 g, 3.5 mmol) obtained in the above-mentioned (3) was dissolved in ether (80 ml), and after cooling to −78° C., 4.8 ml of a hexane solution (n-butyllithium: 7.7 mmol) having an n-butyllithium concentration of 1.6 mol/l was added, followed by stirring at room temperature overnight. Next, ether was distilled off under reduced pressure, and the resulting solid was washed with hexane to obtain dilithium salt (1.15 g) of (1,1'-ethylene)(2,2'-ethylene)-bis(indene). This dilithium salt was dissolved in toluene (30 ml), and the solution was then slowly added to a toluene suspension (50 ml) of zirconium tetrachloride (0.72 g, 3.1 mmol), followed by stirring at room temperature overnight. The reaction solution was filtered, and the filtrate was then concentrated under reduced pressure. The resulting solid was recrystallized from hexane-toluene to obtain (1,1'-ethylene)(2,2'-ethylene)-bis(indenyl)zirconium dichloride. Its yield was 0.60 g, i.e., 38%.

According to ¹H-NMR, the following results were obtained.

¹H-NMR (CDCl₃): 3.50 (d, 4H, —CH₂CH₂—), 3.76 (d, 4H, —CH₂CH₂—), 6.49 (s, 2H, an olefinic proton), 6.90–7.50 (m, 8H, a benzene ring proton)

The structure of this transition metal compound is as follows:

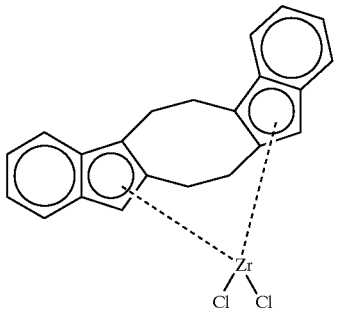

EXAMPLE 9

In a 1-liter autoclave heated and dried were placed 400 ml of toluene and 5 mmol of methylaluminoxane under a nitrogen atmosphere at room temperature. After the temperature of the mixture was raised up to 50° C., 5 micromol of (1,2'-ethylene)(2,1'-ethylene)-bis(indenyl)zirconium dichloride obtained in Example 1-(6) was added thereto, polymerization was then carried out for 30 minutes under pressure raised up to 7 kg/cm² with propylene. After the completion of the polymerization, the reaction product was poured into methanol, and the obtained polymer was collected by filtration and then washed with methanol. After the washing, the polymer was dried by heating under reduced pressure to obtain 24.7 g of a polypropylene. In this case, a catalyst activity was 108.4 kg/g·Zr·hr.

EXAMPLE 10

In a 1-liter autoclave heated and dried were placed 400 ml of toluene and 5 mmol of methylaluminoxane under a nitrogen atmosphere at room temperature. After the temperature of the mixture was raised up to 50° C., 5 micromol of (1,2'-ethylene)(2,1'-ethylene)-bis(indenyl)zirconium dichloride obtained in Example 1-(6) was added thereto, and pressure was raised up to 2 kg/cm² with hydrogen and next up to 7 kg/cm² with propylene. In this state, polymerization was carried out for 30 minutes. After the completion of the polymerization, the reaction product was poured into methanol, and the obtained polymer was collected by filtration and then washed with methanol. After the washing, the polymer was dried by heating under reduced pressure to obtain 183.2 g of a polypropylene. In this case, a catalyst activity was 803.5 kg/g·Zr·hr.

COMPARATIVE EXAMPLE 1

In a 1-liter autoclave heated and dried were placed 400 ml of toluene and 2 mmol of methylaluminoxane under a nitrogen atmosphere at room temperature. After the temperature of the mixture was raised up to 50° C., 5 micromol of rac-ethanediyl-bis(1-indenyl)zirconium dichloride was added thereto, and pressure was then raised up to 7 kg/cm² with propylene. In this state, polymerization was carried out for 30 minutes. After the completion of the polymerization, the reaction product was poured into methanol, and the obtained polymer was collected by filtration and then washed with methanol. After the washing, the polymer was dried by heating under reduced pressure to obtain 32.5 g of a polypropylene. In this case, a catalyst activity was 142.9 kg/g·Zr·hr.

The structure of this transition metal compound is as follows:

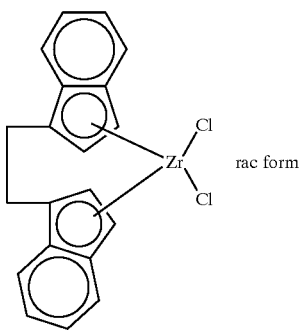

rac form

COMPARATIVE EXAMPLE 2

?In a 1-liter autoclave heated and dried were placed 400 ml of toluene and 2 mmol of methylaluminoxane under a nitrogen atmosphere at room temperature. After the temperature of the mixture was raised up to 50° C., 5 micromol of rac-ethanediyl-bis(1-indenyl)zirconium dichloride was added thereto, and pressure was raised up to 2 kg/cm² with hydrogen and next up to 7 kg/cm² with propylene. In this state, polymerization was carried out for 30 minutes. After the completion of the polymerization, the reaction product was poured into methanol, and the obtained polymer was collected by filtration and then washed with methanol. After the washing, the polymer was dried by heating under reduced pressure to obtain 17.6 g of a polypropylene. In this case, a catalyst activity was 77.4 kg/g·Zr·hr.

Possibility of Industrial Utilization

A transition metal compound of the present invention is a novel double crosslinking type compound, and it is useful as a catalytic component for olefin polymerization. Furthermore, a double crosslinking type biscyclopentadienyl derivative and a double crosslinking type bisindenyl derivative of the present invention can suitably be used as a ligand of the above-mentioned transition metal compound. Moreover, a catalyst for olefin polymerization of the present invention has a high activity and an excellent copolymerizability, and when this catalyst is used, an olefin polymer having a uniform composition and a narrow molecular weight distribution can efficiently be obtained.

What is claimed is:

1. A transition metal compound represented by the general formula (II):

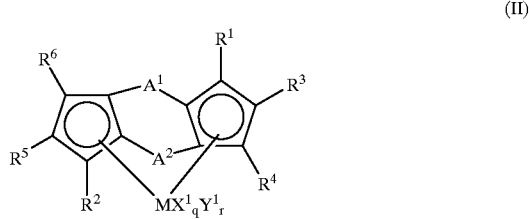

(II)

wherein M is a metallic element in the group 4 of the periodic table; $X^1$ is a σ-bonding ligand, and when a plurality of $X^1$s are present, these plural $X^1$s may be the same or different, and each $X^1$ may crosslink with another $X^1$ or $Y^1$; $Y^1$ is a Lewis base, and when a plurality of $Y^1$s are present, these plural $Y^1$s may be the same or different, and each $Y^1$ may crosslink with another $Y^1$ or $X^1$; $A^1$ and $A^2$ each are independently a crosslinking group selected from the group consisting of methylene group, ethylene group, ethylidene group, propylidene group, isopropylidene group, cyclohexylidene group, 1,2-cyclohexylene group, and vinylidene group; q is an integer of 1 to 5 and equal to the valence of M minus 2; r is an integer of 0 to 3; and $R^1$ to $R^6$ are each a hydrogen atom, a halogen atom, a hydrocarbon group having 1 to 20 carbon atoms, or a halogen-containing hydrocarbon group having 1 to 20 carbon atoms, a silicon-containing group or a hetero-atom-containing group, but at least one of $R^1$ to $R^6$ is not a hydrogen atom, and they may be the same or different, and the adjacent groups of $R^1$ to $R^6$ may bond to each other to form a ring.

2. The transition metal compound according to claim 1, wherein $R^1$ is the same as $R^2$; $R^3$ is the same as $R^5$; and $R^4$ is the same as $R^6$.

3. The transitional metal compound according to claim 1, wherein $A^1$ and $A^2$ are each a methylene group, an ethylene group, or an isopropylidene group.

4. The transition metal compound according to claim 3, wherein each of $A^1$ and $A^2$ is an ethylene group.

5. A transition metal compound represented by the general formula (IV):

(IV)

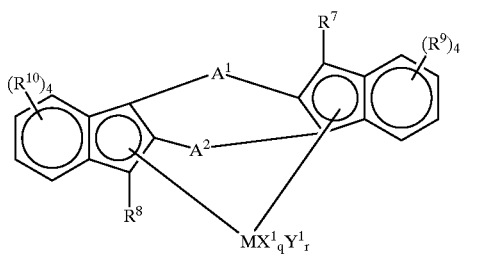

or the following general formula:

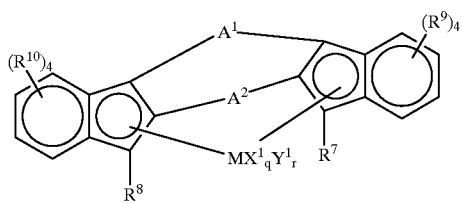

wherein M is a metallic element in group 4 of the periodic table; $X^1$ is σ-bonding ligand, and when a plurality of $X^1$s are present, these plural $X^1$s may be the same or different, and each $X^1$ may crosslink with another $X^1$ or $Y^1$; $Y^1$ is a Lewis base, and when a plurality of $Y^1$s are present, these plural $Y^1$s may be the same or different, and each $Y^1$ may crosslink with another $Y^1$ or $X^1$; $A^1$ and $A^2$ are each a crosslinking group comprising a hydrocarbon group of one or more carbon atoms, and they may be the same or different; q is an integer of 1 to 5 and equal to the valence of M minus 2; r is an integer of 0 to 3; and $R^7$ to $R^{10}$ are each a hydrogen atom, a halogen atom, a hydrocarbon group having 1 to 20 carbon atoms, or a halogen-containing hydrocarbon group having 1 to 20 carbon atoms, a silicon-containing group or a hetero atom-containing group, and they may be the same or different, and the adjacent groups of $R^7$ to $R^{10}$ may bond to each other to form a ring, and four $R^9$s may be the same or different, and four $R^{10}$s may be the same or different.

6. A catalyst for olefin polymerization which comprises a transition metal compound described in claim 5 and an activation cocatalyst.

7. A process for preparing an olefin polymer which comprises the step of homopolymerizing an olefin or copolymerizing an olefin, another olefin and/or another monomer in the presence of a catalyst for polymerization described in claim 6.

8. A catalyst for olefin polymerization which comprises (A) a transition metal compound described in claim 5 and (B) a compound capable of reacting with the transition metal compound of the component (A) or its derivative to form an ionic complex.

9. A catalyst for olefin polymerization according to claim 8 further comprising (C) an organic aluminum compound.

10. A process for preparing an olefin polymer which comprises a step of homopolymerizing an olefin or copolymerizing an olefin, another olefin and/or another monomer in the presence of the catalyst of claim 9.

11. A process for preparing an olefin polymer, which comprises a step of homopolymerizing an olefin or copolymerizing an olefin, another olefin and/or another monomer in the presence of the catalyst of claim 8.

12. The transitional metal compound according to claim 5, wherein $A^1$ and $A^2$ are each represented by the following general formula:

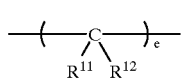

wherein $R^{11}$ and $R^{12}$ are each a hydrogen atom or a hydrocarbon group having 1 to 20 carbon atoms, and $R^{11}$ and $R^{12}$ are the same or different and may bond to each other to form a ring structure; and e is an integer of 1 to 4.

13. The transitional metal compound according to claim 12, wherein $A^1$ and $A^2$ are each a methylene group, an ethylene group, an ethylidene group, a propylidene group, an isopropylidene group, a cyclohexylidene group, a 1,2-cyclohexylene group or a vinylidene group.

14. The transitional metal compound according to claim 13, wherein $A^1$ and $A^2$ are each a methlyene group, an ethylene group, or an isopropylidene group.

15. The transitional metal compound according to claim 14, wherein each of $A^1$ and $A^2$ is an ethylene group.

* * * * *